US006511683B1

(12) United States Patent
Gahler et al.

(10) Patent No.: US 6,511,683 B1
(45) Date of Patent: Jan. 28, 2003

(54) ENCHINACEA SUPPLEMENT AND METHOD OF MANUFACTURE

(75) Inventors: Roland J. Gahler, North Vancouver (CA); Richard E. Barton, Richmond (CA); Jan V. Slama, West Bank (CA); Chuck C. Chang, Vancouver (CA)

(73) Assignee: Factors R & D Technologies Ltd., Calgary (CA)

( * ) Notice: Subject to any disclaimer, the term of this patent is extended or adjusted under 35 U.S.C. 154(b) by 0 days.

(21) Appl. No.: 09/672,729

(22) Filed: Sep. 28, 2000

Related U.S. Application Data

(63) Continuation of application No. PCT/CA00/00931, filed on Aug. 11, 2000.
(60) Provisional application No. 60/157,194, filed on Sep. 30, 1999.

(51) Int. Cl.$^7$ ............................................... A61K 35/78
(52) U.S. Cl. ...................................... 424/737; 424/725
(58) Field of Search .................................. 424/737, 725

(56) References Cited

U.S. PATENT DOCUMENTS

| 5,955,083 A | | 9/1999 | Bonte et al. |
| 6,217,878 B1 | * | 4/2001 | Menon et al. |
| 6,261,565 B1 | | 7/2001 | Empie et al. |

FOREIGN PATENT DOCUMENTS

| CH | 676931 A5 | 3/1991 |
| DE | 37 44570 A1 | 7/1989 |
| DE | 37 44571 A1 | 7/1989 |
| EP | 0 464 298 A1 | 1/1992 |
| WO | WO 98/11778 A1 | 3/1998 |

OTHER PUBLICATIONS

Bauer, R., "Standardisierung von *Echinacea–purpurea*—Prebsaft auf Chicoriensaüre und Alkamide," *Zeitschrift für Phototherapie* 18:270–276, 1997.
Clarke, A., "Healthy and Tasty. Too Good to Be True?" *International Food Ingredients* 5:54–56, 1999.
Stimpel, M., et al., "Polysaccharides From *Echinacea Purpurea* (Eps)—Stimulants With High Macrophage–Specific Properties," *Immunobiology* 165(3–4):359–360, 1983.
Bauer, R., "Analytik und Stanardisierung von Echinacea—Haltigen Phytopharmaka," *Pharmazie in unserer Zeit*, 24:93–95 (1995). (English language summary attached.).
Bauer, R., "Echinacea: Plant Crude Drug on the Way to a Rational Phototherapeutic Agent," *Deutsche Apotheker–Zeitung*, 134:18–27 (1994). (English language summary attached.).
Bauer, R., "Falsche Schlussfolgerunger—Echinacea—haltige Arzneimittel", *Deutsche Apotheker Zeitung*, 138(27):59–60 (1998). (English language summary attached.).
Bauer, R., Jurcic, K., Puhlmann, Jr., and Wagner, H., "Immunological in vivo and in vitro Examinations of Echinacea Extracts," *Arzneimittle–Forschung/Drug Research*, 38:276–281 (1988). (See English language summary, p. 276.).

Beuscher, N. and Kopanski, L., "Stimulation der Immunantwort durch Inhaltsstoffe aus *Baptisia tinctoria*," *Planta Medica*, 51:381–384 (1985). (See English language abstract, p. 381.).
Beuscher, N. Bodinet, C., Willigmann, I., and Egert, D., "Immune Modulating Properties of Root Extracts of Different Echinacea Species," *Zeitchrift fur Phytotherapie*, 16(3):157–166 (1995). (See English language abstract, p. 166).
Beuscher, N. Scheit, K., Bodinet, C., and Kopanski, L., "Immunologically Active Glycoproteins from *Paptisia Tinctoria*," *Planta Medica*, 55:358–363 (1989). (See English language summary, p. 358.).
Blaschek, W., Doll, M., and Franz, G., "Echinacea–Polysaccharides: Analytical Investigations on Pressed Juice and the Preparation Echinacin®," *Zeitschrift fur Phytotherapie*, 19(5):255–262 (1998). (See English language summary, p. 262.).
Braunig, B., Dorn, M., and Knick, E., "Enhancement of Resistance in Common Cold by *Echinacea Purpurea Radix*," *Zeitschrift fur Phytotherapie*, 13:7–13 (1992). (See English language summary attached.).
Bukovsky,, M., Kostalova, D., Magnusova, R., and Vaverkova, S., "Immunomodulatory Activity of Ethanol–Water Extracts from Aerial parts of Plants of *Echinacea Moench* and *Rudbeckia L.*," *Ceskoslovenska Farmachie*, 42(5):228–231, 193 (1993) (See English language summary, p. 228.).
Dorsch, W., "Clinical Applications of Extracts of *Echinacea Purpurea* and *Echinacea Pallida*. Critical Evaluation of Controlled Clinical Studies," *Zeitschrift fur Arztliche Fortbildung*, 90(2):117–122 (1996). (See English language abstract, p. 121.).

(List continued on next page.)

*Primary Examiner*—Christopher R. Tate
*Assistant Examiner*—Randall Winston
(74) *Attorney, Agent, or Firm*—Christensen O'Connor Johnson Kindness PLLC

(57) ABSTRACT

In one aspect, the present invention provides Echinacea compositions including standardized amounts of at least two Echinacea components. More preferably the Echinacea compositions of the present invention include standardized amounts of at least three Echinacea components. Presently preferred Echinacea components are cichoric acid, Echinacea alkylamides and Echinacea polysaccharides. In another aspect, the present invention provides methods for preparing Echinacea compositions, the methods including the step of combining amounts of at least two Echinacea components, preferably three Echinacea components, sufficient to yield an Echinacea composition including standardized amounts of each of the combined Echinacea components. In yet another aspect, the present invention provides Echinacea extracts, and methods for preparing Echinacea extracts. Presently preferred Echinacea extracts are enriched in one or more members of the group consisting of polysaccharides, alkylamides and cichoric acid. In yet another aspect, the present invention provides methods for enhancing immune system activity in a mammal.

6 Claims, 8 Drawing Sheets

OTHER PUBLICATIONS

Fleischhacker, R., "Echinacea als Immunstimulans," *Deutsche Apotheker Zeitung*, 138(20):54–57 (1998). (See English language summary attached.).

Gaisbauer, M. Schleich, Th., Stickl, H., and Wilczek, I., "Phagocytic Activity of Granulocytes Using Chemiluminescence Measurement," *Arzneimittle–Forschung/Drug Research*,40:594–598 (1990). (See English language summary, p. 594.).

Heinzer, F., Chavanne, M., Meusy, J., Maitre, H., Giger, E., and Baumann, T., "Ein Beitrag zur Klassifizierung der Therapeutisch Verwendten Arten der Gattung Echinacea," *Pharmaceutica Acta Helvetiae*, 63:132–136 (1998). (See English language summary attached.).

Jurcic, K., Melchart, D., Holzmann, M., Martin, P., Bauer, R., Doenecke, A., and Wagner, H., "Two Proband Studies for the Simulation of Granulocyte Phagocytosis by Echinacea-Containing Preparations," *Zeitchrift fur Phytotherapie*, 10(2):67–70 (1989). (See English language summary, p. 70.).

Kosalec, I., "History and Future of Echinacea Species—Natural Immunostimulating Plants", *Faraceutski Glannik*, 54(5):161–170 (1998). (See English language summary, p. 169.).

Lohmann–Matthes, M. and Wagner, H., "Machrophage Activation by Plant Polysaccharides," *Zietschrift fur Phytotherapie*, 10(2):52–59 (1989). (See English language summary, p. 59.).

Schoneberger, D., "Einfluss der Immunostimulierenden Wirkung von Press–saft aus Herba *Echinaceae Purpureae* auf Verlauf und Scheregrad von Erkaltungskrankheiten," *Forum Immunologie*, 8:2–12 (1992). (See English language summary attached.).

Schumacher, A., and Friedberg, K.D., "Analysis of the Effect of *Echinacea Angustifolia* on Unspecified Immunity of the Mouse," *Arzeimittle–Forschung/Drug Research*, 41:141–147 (1991). (See English language summary, p. 141.).

Soicke, H., Al–Hassan, G., and Gorler, K., "Further Derivatives of Caffeic Acid from *Echinacea Purpurea*," *Planta Medica*, 54:176–176 (1988). (See English language abstract, p. 175.).

Wacker, A. and Hilbig, W., "Virus–Inhibition by *Echinacea Purpurea*," *Planta Medica*, 33:89–102 (1978). (English language abstract only, p. 89.).

Wagner, H., Jurcic, K., "Immunological Studies of Plant Extract Combinations in vitro and in vivo on the Stimulation of Phatocytosis," *Arzneimittel–Forschung/Drug Research*, 41(10):1072–1076 (1991). See English language summary, p. 1072.).

Wagner, H., Jurcic, K., Doenicke, A., Rosenhuber, E., Behrens, N., "Influence of Homeopathic Drug Preparations on Phagocytic Activity of Human Granulocytes/In Vitro Tests and Controlled Single–Blind Studies," *Arzneimittel Forschung/Drug Research*, 36(II):1421–1425 (1986). (See English language summary, p. 1421.).

Wagner, H., Proksch, A., Reiss–Mauer, I., Vollmar, A., Odenthal, H., Stuppner, H., Jurcic, K., Le Turdu, M., and Heur, Y., "Immunostimulating Polysaccharides (Heteroglycanes) of Higher Plants/Preliminary Communication," *Arzneimittle–Forschung/Drug Research*, 34:659–661 (1984). (See English language summary, p. 1069.).

Wagner, H., Proksch, A., Reiss–Maurer, I., Vollmar, A., Odenthal, S., Stuppner, H., Jurcic, K., Turdu, M., and Fang, J., "Immunostimulating Polysaccharides (Heteroglycanes) of Higher Plants," *Arzneimittel Forschung/Drug Research*, 35:1069–1073 (1985). (See English language summary, p. 659.).

Wagner, H., Stuppner, H., Puhlmann, J., Jurcic, K., and Zenk, M., "Immunstimulierend wirkende Pokysaccharide aus Zellkulturen von *Echinacea Purpurea* (L.) *Moench*," *Zeitschrift fur Phytotherapie*, 8:125–126 (1987). (See English language summary attached.).

Wagner, H., Stuppner, H., Puhlmann, Jr., Brummer, B., and Zenk, M., "Isolation of Immunologically Active Polysaccharides for Echinacea–Drugs and Tissue Culture," *Zeitschrift fur Pytotherapie*, 10(2):35–38 (1989). (See English language summary, p. 38.).

Wildfeuer, A. and Mayerhofer, D., "Study of the Influence of Phytopreparations of the Cellular Functions of Body Defense," *Arzneimittel Forschung/Drug Research*, 44(1)3:361–366 (1994). (See English language summary, p. 362.).

Avedikian, J., Herbs: "What are They . . . and do they Work?" *California Pharmacist*, 42:15 (1994).

Awang, A. and Kindack, D., "Herbal Medicine: Echinacea," *Canadian Pharmaceutical Journal*, 124:512–516 (1991).

Bauer, R. and Foster, S., "Analysis of Alkamides and Caffeic Acid Derivatives from *Echinacea simulata* and *E. paradoxa* Roots," *Planta Medica*, 57:447–449 (1991).

Bauer, R. and Foster, S., "HPLC Analysis of *Echinacea simulata* and *E. paradoxa* Roots," *Planta Medica*, 55:637 (1989).

Bauer, R. and Remiger, P., "TLC and HPLC Analysis of Alkamides in Echinacea Drugs," *Planta Medica*, 55:367–371 (1989).

Bauer, R. and Tittel, G., "Quality Assessment of Herbal Preparations as a Precondition of Pharmacological and Clinical Studies," *Phytomedicine*, 2(3):193–198 (1996).

Bauer, R. and Wagner, H., "Echinacea Species as Potential Immunostimulatory Drugs," *Economic and Medicinal Plant Research*, 5:253–321 (1991).

Bauer, R., "Active Principles and Biological Effects of Echinacea," Report of a talk given in Orlando, Florida (1996).

Bauer, R., "Echinacea Containing Drugs—Effects and Active Constituents," *Zeitschrift fur Arztliche Fortbildung*, 90(2):111–115 (1996).

Bauer, R., "The Echinacea Story—The Scientific Development of an Herbal Immunostimulant," *Plants for Food and Medicine, Proceedings of the Joint Conference for Economic Botany*, pp. 317–3323 (Jul. 1–6, 1996).

Bauer, R., Khan, I., Wagner, H., "TLC and HPLC Analysis of *Echinacea pallida* and *E. augustifolia* Roots," *Planta Medica*, 54:426–430 (1988).

Bauer, R., Khan, I., Wray, V., and Wagner, H., "Two Acetylenic Compounds from *Echinacea pallida* Roots," *Phytochemistry* 26(4):1198–1200 (1987).

Bauer, R., Remiger, P., and Wagner, H., "Alkamides from the Roots of *Echinacea augustifolia*," *Phytochemistry*, 28(2):505–508 (1989).

Bauer, R., Remiger, P., and Wagner, W., "Alkamides from the Roots of *Echinacea purpurea*," *Phytochemistry*, 27(7):2339–2342 (1988).

Beuscher, N., Beuscher, H., and Bodinet, C., "Enhanced Release of Interleukin–1 from Mouse Macrophages by Glycoproteins and Polysaccharides from *Baptisia tinctoria* and Echinacea Species," *Planta Medica*, 55:660 (1989).

Beuscher, N., Kopanski, L., and Ernwein, C., "Modulation of Immune Response by Polymeric Substances from *Baptisia tinctoria* and *Echinacea augustifolia*," *Advances in the Biosciences*, 68:329–336 (1988).

Beuscher, N., Scheit, K., Bodinet, C., and Egert, D., "Modulation of Host Resistance by Polymeric Substances from *Baptisia trinctoria* and *Echinacea purpurea*," *Immunotherapeutic Prospects of Infectious Diseases*, pp. 59–63 (1990).

Bodinet, C. and Beuscher, N., "Antiviral and Immunological Activity of Glycoproteins from *Echinacea purpurea radix*," *Planta Medica*, 57(Supplemental Issue 2):A33–A34 (1991).

Bohlmann, F. and Hoffmann, H., "Further Amides from *Echinacea purpurea*," *Phytochemistry*, 22(5):1173–1175 (1983).

Bone, K., "Echinacea: What Makes it Work?" *Alternative Medicine Review*, 2(2):87–93 (1997).

Brinkeborn, R., Shah, D., and Degenring, F., "Echinaforce® and other Echinacea Fresh Plant Preparations in the Treatment of the Common Cold," *Phytomedicine*, 6(1):1–5 (1999).

Brinker, F., *Herb Contraindications and Drug Interactions*, 2nd Ed., Eclectic Medical Publications, pp. 67–69 (1998).

Budzianowski, J., "Coumarins, Caffeoyltartaric Acids and Their Artificial Esters from *Taraxacum officinale* Leaves," *Planta Medica*, 63:288 (1997).

Bukovsky, M., Vaverkova, S., and Kost'alova, D., "Immunomodulating Activity of *Echinacea gloriosa* L., *Echinacea angustofolia* DC, and *Rubdeckia speciosa* Wenderoth Ethanol–Water Extracts," *Polish Journal of Pharmacology*, 47(2):175–177 (1995).

Burger, R., Torres, A., Warren, R., Caldwell, V., and Hughes, B., "Echinacea–Induced Cytokine Production by Human Macrophages," *International Journal of Immunopharmacology*, 19(7):371–379 (1997).

Cheminat, A., Zawatzky, R., Becker, H., and Brouillard, R., "Caffeoyl Conjugates from Echinacea Species: Structures and Biological Activity," *Phytochemistry*, 27(9):2787–2794 (1988).

Dorn, M., Knick, E., and Lewith, G., "Placebo–Controlled, Double–Blind Study of *Echinaceae pallidae radix* in Upper Respiratory Tract Infections," *Complementary Therapies in Medicine*, 5(1):40–42 (1997).

El–Gengaihi, S., Shalaby, A., Agina, E., and Hendawy, S., "Alkylamides of *Echinacea purpurea* L. as Influenced by Plant Ontogony and Fertilization," *Journal of Herbs, Spices & Medicinal Plants*, 5(4):35–41 (1998).

Elsasser–Beile, U., Willenbacher, W., Bartsch, H., Gallati, H., Schule Monting, Jr., von Kleist, S., "Cytokine Production in Leukocyte Cultures During Therapy with Echinacea Extract," *Journal of Clinical Laboratory Analysis*, 10(6):441–445 (1996).

Erhard, M., Kellner, J., Wild, J., and Losch, U., "Effect of Echinacea, Aconitum, Lachesis, and Apis Extracts, and their Combinations on Phagocytosis of Human Granulocytes," *Phytotherapy Research*, 8:14–17 (1994).

Facino, R., Carini, M., Aldini, G., and Marinello, C., Arlandini, E., Franzoi, L., and Colombo, M., "Direct Characterization of Caffeoyl Esters with Antihyaluronidase Activity in Crude Extracts from *Echinacea augustifolia* Roots by Fast Atom Bombardment Tandem Mass Spectroscopy," *Il Farmaco*, 48(10):1447–1461 (1993).

Facino, R., Carini, M., Aldini, G., Saibene, L., Pietta, P., and Maurt, P., "Echinacoside and Caffeoyl Conjugates Protect Collagen from Free Radical–Induced Degradation: A Potential Use of Echinacea Extracts in the Prevention of Skin Photodamage," *Planta Medica*, 61(6):510–514 (1997).

Glowniak, K., Zgorka, G., and Kozyra, M., "Solid–Phase Extraction and Reversed–Phase high–performance Liquid Chromatography of Free Phenolic Acids in Some Echinacea Species," *Journal of Chromatography A.*, 730:25–29 (1996).

Greger, H. "Alkamides: Structural Relationships, Distribution and Biological Activity," *Planta Medica*, 50(5):366–375 (1984).

Grimm, W. and Muller, H., "A Randomized Controlled Trial of the Effect of Fluid Extract from *Echinacea purpurea* on the Incidence and Severity of Colds and Respiratory Infections," *The American Journal of Medicine*, 106(2):138–143 (1999).

Hamburger, M. and Hostettmann, K., "Analytical Aspects of Drugs of Natural Origin," *Journal of Pharmaceutical and Biomedical Analysis*, 7(12):1337–1349 (1989).

He, X., Lin, L., Bernart, M., and Lian, L., "Analysis of Alkamides in Roots and Achenes of *Echinacea purpurea* by Liquid Chromatography–Electropspray Mass Spectrometry," *Journal of Chromatography A*, 815:205–211 (1998).

Heinzer, F., Meusy, J., and Chavanne, M., "*Echinacea pallida* and *Echinacea purpurea:* Follow–up of Weight Development and Chemical Composition for the First Two Culture Years," *Planta Medica*, 55:221 (1989).

Hobbs, C., Echinacea: "A Literature Review," Special Supplement to *HerbalGram #30*, 33–48 (1994).

Hobbs, C., *Echinacea: The Immune Herb!*, Botanica Press (1990).

Houghton, P., "Herbal Products Part 3: Echinacea," *The Pharmaceutical Journal*, 253:342–343 (1994).

Ingolfsdottir, K., Jurcic, K., and Wagner, H., "Immunomodulating Polysaccharides from Aqueous Extracts of *Cetraria inlandica* (Iceland Moss)," *Phytomedicine*, 5(5):333–339 (1998).

Li, T., "Echinacea: Cultivation and Medicinal Value", *HortTechnology*, 8(2):122–129 (1998).

Lienert, D., Anklam, E., and Panne, U., "Gas Chromatography–Mass Spectral Analysis of Roots of Echinacea Species and Classification by Multivariate Data Analysis," *Phytochemical Analysis*, 9:88–98 (1998).

Luettig, B., Steinmuller, C., Gifford, G., Wagner, H., and Lohmann–Matthes, L., "Macrophage Activation by the Polysaccharide Arabinoglactan Isolated from Plant Cell Cultures of *Echinacea purpurea*," *Journal of the National Cancer Institute*, 81:669–675 (1989).

Melchart, D., Linde, K., Worku, F., Sarkady, L., Holzmann, M., Jurcic, K., Wagner, H., "Results of Five Randomized Studies on the Immunomodulatory Activity of Preparations of Echinacea," *Journal of Alternative and Complementary Medicine*, 1(2):145–160 (1995).

Mengs, U., Clare, C., and Poiley, J., "Toxicity of *Echinacea purpurea*: Acute Subacute and Genotoxicity Studies," *Arzneimittel–Forschung/Drug Research,* 41 II(10):1076–1081 (1991).

Miller, L., "Herbal Medicinals—Selected Clinical Considerations Focusing on Known or Potential Drug Interactions," *Archives of Internal Medicine,* 158(20):2200–2221 (1998).

Molinatorres, J., Salgado–Garciglia, Ramirez–Chavez, E., and Del Rio, R., "Purely Olefinic Alkamides in *Heliopsis longipes* and *Acmella* (*Spilanthes*) *oppositifolia,*" *Biochemical Systematics and Ecology,* 24(1):43–47 (1996).

Mose, R., "Zur Wirkung von Echinacin auf Phagozytoseaktivitat und Natural Killer Cells," *Medizinische Welt,* 34(51–52):1463–1467 (1983).

Mowrey, D.B., *Echinacea—How An Amazing Herb Supports and Stimulates Your Immune System,* Keats Publishing Inc. (1996).

Muller, J. and Clauson, K., Pharmaceutical Considerations of Common Herbal Medicine, *American Journal of Managed Care,* 3(11):1753–1770 (1997).

Muller–Jakic, B., Breu, W., Probstle, A., Redl, K., Greger, H., and Bauer, R., "In Vitro Inhibition of Cyclooxygenase and 5–Lipooxygenase by Alkamides from Echinacea and Achillea Species," *Planta Medica,* 60:37–40 (1994).

Murray, M., *The Healing Power of Herbs,* 2nd Ed., Prima Publishing, pp. 92–107 (1995).

Mustea, I., Prostescu, I., Tamas, M., and Rasnita, T., "Experimental Evaluation of Protective Activity of *Echinacea Pallida* Against Cisplatin Toxicity," *Phytotherapy Research,* 11(3):263–265 (1997).

Newall, C., Anderson, L., Phillipson, Jr., *Herbal Medicines—A Guide for Health–Care Professionals,* The Pharmaceutical Press, pp. 101–103 (1996).

Parnham, M.J., "Benefit–Risk Assessment of the Squeezed Sap of the Purple Coneflower (*Echinacea purpurea*) for Long Term Oral Immunostimulation," *Phytomedicine,* 3(1):95–102 (1996).

Pepping, J., "Alternative Therapies—Echinacea," *American Journal of Health–System Pharmacy,* 56(2):121–122 (1999).

Perry, N., van Klink, J., Burgess, E., and Parmenter, G., "Alkamide Levels in *Echinacea purpurea*: A Rapid Analytical Method Revealing Differences Among Roots, Rhizomes, Stems, Leaves and Flowers," *Planta Medica,* 63(1):58–62 (1997).

Pietta P., Mauri, P., and Bauer, R., "MEKC Analysis of Different Echinacea Species," *Planta Medica,* 64(7):649–652 (1998).

Proksch, A. and Wagner, H., "Structural Analysis of a 4–O–Methyl–Glucuronarabinoxylan with Immuno–Stimulating Activity from *Echinacea purpurea,*" *Phytochemistry,* 26:1989–1993 (1987).

Robinson, Jr., W., "L–Chicoric Acid, An Inhibitor of Human Immunodeficiency Virus Type 1 (HIV–1) Integrase, Improves on the in vitro Anti–HIV–1 Effect of Zidovudine Plus a Protease Inhibitor (AG1350)," *Antiviral Research,* 39:101–111, (1998).

Robinson, W., Reinecke, M., Abdel–Malek, S., Jia, Q., and Chow, S., "Inhibitor of HIV–1 Replication that Inhibit HIV Integrase," *Proceedings of the National Academy of Sciences (PNAS),* 93:6326–6331 (1996).

Roesler, J., Emmendorffer, A., Steinmuller, C., Luettig, B., Wagner, H., and Lohmann–Matthes, M., "Application of Purified Polysaccharides from Cell Cultures of the Plant *Echinacea purpurea* to Test Subjects Mediates Activation of the Phagocyte System," *International Journal of Immunopharmacology,* 13(7):931–941 (1991).

Roesler, J., Steinmuller, C., Kiderlen, A., Emmendorffer, A., Wagner, H., Lohmann–Matthes, M., "Application of Purified Polysaccharides from Cell Cultures of the Plant *Echinacea purpurea* to Mice Mediates Protection Against Systemic Infections with *Listeria monocytogenes* and *Candida albicans,*" *International Journal of Immunopharmacology,* 13(1):27–37 (1991).

Rogers, K., Grice, I., Mitchell, C., and Griffiths, L., "High Performance Liquid Chromatography Determined Alkamide Levels in Australian–Grown Echinacea spp.," *Australian Journal of Experimental Agriculture,* 38:403–408 (1998).

Rosario, S., da Silva, A., and Parente, J., "Alkamides from *Cissampelos glaberrima,*" *Planta Medica,* 62:376–377 (1996).

Scaglione, F. and Lund, B., "Efficacy in the Treatment of the Common Cold of a Preparation Containing Echinacea Extract," *International Journal of Immunotherapy,* 11(4):163–166 (1995).

Scarpati, M. and Oriente, G., "Chicoric Acid (Dicaffeyltartaric Acid): Its Isolation From Chicory (*Chicorium intybus*) and Synthesis," *Tetrahedron,* 4:43–48 (1958).

Schulthess, B., Giger, E., and Baumann, T., "Echinacea: Anatomy, Phytochemical Pattern, and Germination of the Achene," *Planta Medica,* 57:384–388 (1988).

See, D.M., Broumand, N., Sahl, L., and Tilles, J., "In Vitro Effects of Echinacea and Ginseng on Natural Killer and Antibody–Dependent Cell Cytotoxicity in Healthy Subjects and Chronic Fatigue Syndrome or Acquired Immunodeficiency Syndrome Patients," *Immunopharmacology,* 35:229–235 (1997).

Shida, T., Yagi, A., Nisimura, H., and Nishioka, I., "Effect of Aloe Extract on Peripheral Phagocytosis in Adult Bronchial Asthma," *Planta Medica,* 51:273–275 (1985).

Skwarek, T., Tynecka, Z., Glowniak, K., and Lutostanska, E., "Echinacea L.—Inducer of Interferons," *Herba Polonica,* 41(2):110–117 (1996).

Steinmuller, C., Roesler, J., Grottrup, E., Franke, G., "Polysaccharides Isolated from Plant Cell Cultures of *Echinacea purpurea* Enhance the Resistance of Immunosuppressed Mice Against Systemic Infections with *Candida albicans* and *Listeria monocytogenes,*" *International Journal of Immunopharmacology,* 15(5):605–614 (1993).

Stimpel, A., Proksch, A., Wagner, H., and Lohmann–Matthes, M., "Macrophage Activation and Induction for Macrophage Cytotoxicity by Purified Polysaccharide Fractions from the Plant *Echinacea purpurea,*" *Planta Medica,* 65(1):175–177 (1999).

Stotzem, C., Hungerland, U., and Mengs, U., "Influence of *Echinacea purpurea* on the Phagocytosis of Human Granulocytes," *Medical Science Research,* 20(19):719–720 (1992).

Sumaryono, W., Proksch, P., Wray, V., Witte, V., and Hartmann, T., "Qualitative and Quantitative Analysis of the Phenolic Constituents from *Orthosphon aristatus,*" *Planta Medica,* 57(2):176–180 (1991).

Swaef, S., DeBeer, J., and Vlietinck, J., "Quantitative Determination of p–Coumaric Acid in *Echinacea purpurea* Press Juice and Urgenin. A validated Method," *Journal of Liquid Chromatography,* 17(19):4169–4183 (1994).

Thom, E. and Wollan, T., "A Controlled Clinical Study of Kanjang Mixture in the Treatment of Uncomplicated Upper Respiratory Tract Infections," *Phytotherapy Research,* 2:207–210 (1997).

Tragni, E., Galli, A., Tubaro, A., Del Negro, P., and Loggia, R., "Anti–inflammatory Activity of *Echinacea augustifolia* Fractions Separated on the Basis of Molecular Weight," *Pharmacological Research Communications,* 20(Suppl. 5):87–90 (1988).

Tragni, E., Tubaro, A., and Gali, C., "Evidence from Two Classic Irritation Tests for an Anti–inflammatory Action of the Natural Extract, Echinacea B," *Food and Chemical Toxicology,* 23:317–319 (1985).

Trypsteen, M., Van Lijsebettens, M., Van Severen, R., and Van Montagu, M., "*Agrobacterium rhizogenes*–mediated Transformation of *Echinacea purpurea,*" *Plant Cell Reports,* 10:85–89 (1991).

Tubaro, A. Tragni, E., Del Negro, P., Galli, C., and Della Loggia, R., "Anti–inflammatory Activity of a Polysaccharide Fraction of *Echinacea augustifolia,*" *Journal of Pharmacy and Pharmacology* 39:567–569 (1987).

Tyler, V., *Herbs of Choice—The Therapeutic Use of Phytochemicals,* Pharmaceutical Products Press, pp. 182–184 (1994).

Voaden, D. and Jacobson, M., "Tumor Inhibitors. 3. Identification and Synthesis of an Oncolytic Hydrocarbon from American Coneflower Roots," *Journal of Medicinal Chemistry,* 15(6):619–623 (1972).

Wagner, H. and Proksch, A., "Immunostimulatory Drugs of Fungi and Higher Plants," *Economic and Medicinal Plant Research,* 1:113–153 (1985).

Wagner, H., "Search for New Plant Constituents with Potential Antiphilogistic and Antiallergic Activity," *Planta Medica,* 55:235–241 (1989).

Wagner, H., Stuppner, H., Schafer, W., and Zenk. M., "Immunologically Active Polysaccharides of *Echinacea purpurea* Cell Cultures," *Phytochemistry,* 27(1):119–126 (1988).

Wagner, Hildebert, "Immunosimulants of Plant Origin," *Croatica Chemica Acta,* 68(3):615–626 (1995).

Yagi, A., Hamada, K., Mihashi, K., Harada, N., and Nishioka, I., "Structure Determination of Polysaccharides in *Aloe saponaria* (Hill.) Haw. (Liliaceae)," *Journal of Pharmaceutical Sciences,* 73:62–65 (1984).

Yagi, A., Nishimura, H., Shida, T., and Nishioka, I., "Structure Determination of Polysaccharides in *Aloe arborescens* var. *natalensis,*" *Planta Medica,* 52:213–218 (1986).

Yasuda, I., Takeya, K., and Itokawa, H., "Structures of Amides from *Asiasarum heterotropoides,*" *Chemical and Pharmaceutical Bulletin,* 29(2):564–566 (1981).

Zdero, C., Bohlmann, F., King, R., and Lander, N., "An Isobutylamide and Beyerene Derivatives from Brachycome Species," *Phytochemistry,* 27(9):2984–2985 (1988).

Zink, T., Chaffin, J., "Herbal 'Health' Products: What Family Physicians Need to Know," *American Family Physician,* 58(5):1133–1140 (1998).

Bergner, P., *The Healing Power of Echinacea, Goldenseal, and Other Immune System Herbs,* Prima Publishing, pp. 1–169 (1997).

Foster, S., Echinacea: *Nature's Immune Enhancer,* Healing Arts Press (1991).

Hobbs, C., *Echinacea: The Immune Herb!,* Revised Edition, Botanica Press (1990, 1995).

Upton, R., *Echinacea,* Keats Publishing Inc. (1997).

\* cited by examiner

ENCHINACEA SUPPLEMENT AND METHOD OF MANUFACTURE

RELATED APPLICATIONS

The present application is a continuation of co-pending International Patent Application Number PCT/CA00/00931, filed Aug. 11, 2000, which relates to and claims the benefit of priority from co-pending U.S. Provisional patent application Ser. No. 60/157,194, filed Sep. 30, 1999, the benefit of which is hereby claimed under 35 U.S.C. §§119 and 120.

FIELD OF THE INVENTION

The present invention relates to nutritional supplements prepared from plants of the genus Echinacea.

BACKGROUND OF THE INVENTION

Numerous studies attest to the health-promoting properties of extracts derived from plants of the genus Echinacea. See, e.g., A. Awang & D. Kindack, *Canadian Pharmaceutical Journal*, 124: 512–516 (1991). There is a strong commercial market for Echinacea compositions containing biologically active components that are believed to promote good health. Further, it is desirable to formulate Echinacea compositions to contain standardized amounts of biologically active components derived from Echinacea plants. Such standardized, Echinacea compositions provide the consumer with a consistent, effective dose of one or more, biologically active, Echinacea components.

In particular, there is a strong commercial market for Echinacea extracts containing a high concentration of one or more, biologically active, Echinacea components believed to promote good health. Such highly enriched extracts can be used directly as dietary supplements, or can be blended with other Echinacea extracts to prepare dietary supplements containing standardized amounts of biologically active, Echinacea components.

Scientific studies indicate that Echinacea-derived polysaccharides, alkylamides and cichoric acid (a caffeic acid derivative also known as chicoric acid, 2,3-o-dicaffeoyl-tartaric acid) each possess health-promoting properties. For example, alkylamides from Echinacea have been shown to stimulate phagocytosis in mice granulocytes at concentrations of about 0.1 parts per million (ppm). Bauer, R. et al., *Arzneim.-Forsch./Drug Research*, 38: 276–281 (1988). Similarly, cichoric acid has been shown to increase phagocytosis in granulocytes, and may stimulate the immune system at concentrations as low as 0.01 ppm. See e.g., A. Awang et al., supra. Echinacea polysaccharides have been shown to inhibit hyaluronidase, increase phagocytosis, induce the release of interferon-6, and enhance resistance to *C. albicans* infection in mice. See, e.g., A. Awang et al., supra; Wagner, H, et al. *Arzneim.-Forsch./Drug Research*, 35: 1069–1075 (1985).

Numerous factors must be considered and optimized in order to produce Echinacea extracts having a high concentration of polysaccharides, alkylamides and/or cichoric acid. For example, the amounts of polysaccharides, alkylamides and cichoric acid in Echinacea plants are influenced by the species of the plant, the age of the plant and the plant growth conditions. Additionally, the solvents and process parameters, such as temperature and length of extraction period, utilized to extract polysaccharides, alkylamides and cichoric acid from Echinacea plants can greatly affect the yield of these components.

Thus, there is a need for methods for efficiently extracting polysaccharides, alkylamides and cichoric acid from Echinacea plants, and for Echinacea extracts containing a high concentration of polysaccharides, alkylamides and/or cichoric acid. Further, there is a need for standardized Echinacea compositions containing a predetermined, desired amount of Echinacea extracts, including polysaccharide, alkylamide and/or cichoric acid extracts.

SUMMARY OF THE INVENTION

In one aspect, the present invention provides Echinacea compositions including standardized amounts of at least two Echinacea components. More preferably the Echinacea compositions of the present invention include standardized amounts of at least three Echinacea components. In this context the term "standardized amount", or grammatical equivalents thereof, means a desired, quantified amount of an Echinacea component. Presently preferred Echinacea components are Echinacea polysaccharides, Echinacea alkylamides and cichoric acid. Presently preferred Echinacea extracts useful for preparing the Echinacea compositions of the present invention are extracts enriched in cichoric acid (most preferably cichoric acid prepared in accordance with the present invention), Echinacea alkylamides (most preferably Echinacea alkylamides prepared in accordance with the present invention) or Echinacea polysaccharides (most preferably Echinacea polysaccharides prepared in accordance with the present invention). The Echinacea compositions of the present invention can be in liquid form, gel form or solid form, such as a powder, or tablets, or capsules, and are preferably adapted for administration (more preferably oral administration) to a human being.

In another aspect, the present invention provides methods for preparing Echinacea compositions, the methods including the step of combining amounts of at least two Echinacea components, preferably three Echinacea components, sufficient to yield an Echinacea composition including standardized amounts of each of the combined Echinacea components. In this context the term "standardized amount", or grammatical equivalents thereof, means a desired, quantified amount of an Echinacea component. Presently preferred Echinacea components are Echinacea polysaccharides, Echinacea alkylamides and cichoric acid. Presently preferred Echinacea extracts useful for preparing the Echinacea compositions of the present invention are extracts enriched in cichoric acid (most preferably cichoric acid prepared in accordance with the present invention), Echinacea alkylamides (most preferably Echinacea alkylamides prepared in accordance with the present invention) or Echinacea polysaccharides (most preferably Echinacea polysaccharides prepared in accordance with the present invention).

In another aspect, the present invention provides methods for preparing Echinacea extracts enriched in at least one Echinacea component. The methods of the present invention for preparing enriched Echinacea extracts include the steps of selecting an Echinacea plant at a developmental stage having an enhanced amount of a desired component (such as cichoric acid, alkylamides or polysaccharides); selecting a portion of the plant that is enriched in the desired component, and contacting the selected portion with an amount of a solvent, selected from the group consisting of ethanol and water, effective to extract the desired component from the plant portion. Preferably the Echinacea extract is then concentrated. Any species of Echinacea plant can be utilized in the practice of the present invention, but the presently preferred species is *E. purpurea*. Extraction of Echinacea plant material utilizes a ratio (by weight) of plant material to solvent of no more than about two parts plant material to about one part solvent. The presently preferred ratio (by weight) of plant material to solvent is about one part plant material to about four parts solvent.

In yet another aspect, the present invention provides liquid Echinacea extracts enriched in one or more member of the group consisting of Echinacea polysaccharides, Echinacea alkylamides and cichoric acid. Presently preferred liquid Echinacea extracts enriched in polysaccharides include polysaccharides at a concentration greater than about 1% (w/w), more preferably greater than about 5% (w/w), most preferably greater than about 10% (w/w). Presently preferred liquid Echinacea extracts enriched in alkylamides include alkylamides at a concentration greater than about 0.1% (w/w), more preferably greater than about 1.0% (w/w), most preferably greater than about 3.0% (w/w). Presently preferred liquid Echinacea extracts enriched in cichoric acid include cichoric acid at a concentration greater than about 0.2% (w/w), more preferably greater than about 0.5% (w/w), most preferably greater than about 3.0% (w/w).

In yet another aspect, the present invention provides solid Echinacea extracts enriched in one or more member of the group consisting of Echinacea polysaccharides, Echinacea alkylamides and cichoric acid. Presently preferred solid Echinacea extracts enriched in polysaccharides include polysaccharides at a concentration greater than about 0.01% (w/w), more preferably greater than about 0.05% (w/w), most preferably greater than about 20% (w/w). Presently preferred solid Echinacea extracts enriched in alkylamides include alkylamides at a concentration greater than about 0.001% (w/w), more preferably greater than about 0.01% (w/w), most preferably greater than about 0.5% (w/w). Presently preferred solid Echinacea extracts enriched in cichoric acid include cichoric acid at a concentration greater than about 0.005% (w/w), more preferably greater than about 0.05% (w/w), most preferably greater than about 1.5% (w/w).

The Echinacea extracts of the present invention are useful, for example, as dietary supplements and as sources of polysaccharides, alkylamides or cichoric acid for blending to produce the Echinacea compositions of the present invention. The Echinacea compositions of the present invention are useful, for example, as human dietary supplements. By way of non-limiting example, when administered to a mammal the Echinacea compositions and extracts of the invention stimulate one or more of the following aspects of the immune system: macrophage phagocytic activity; nitric oxide production by macrophages; TNF-α production by macrophages; IFN-γ production by splenocytes; and TNF-α production by splenocytes.

In yet another aspect, the present invention provides methods for enhancing immune system activity in a mammal. In one embodiment, the methods comprise administering to a mammal an effective daily dosage of an Echinacea composition comprising standardized amounts of Echinacea cichoric acid, Echinacea alkylamides and Echinacea polysaccharides. In another embodiment, the methods comprise administering to the mammal an effective daily dosage of an Echinacea extract selected from the group consisting of Echinacea alkylamides and Echinacea polysaccharides. The term "effective daily dosage," and grammatical equivalents thereof, means a daily dosage that is effective to enhance immune system activity in a mammal.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
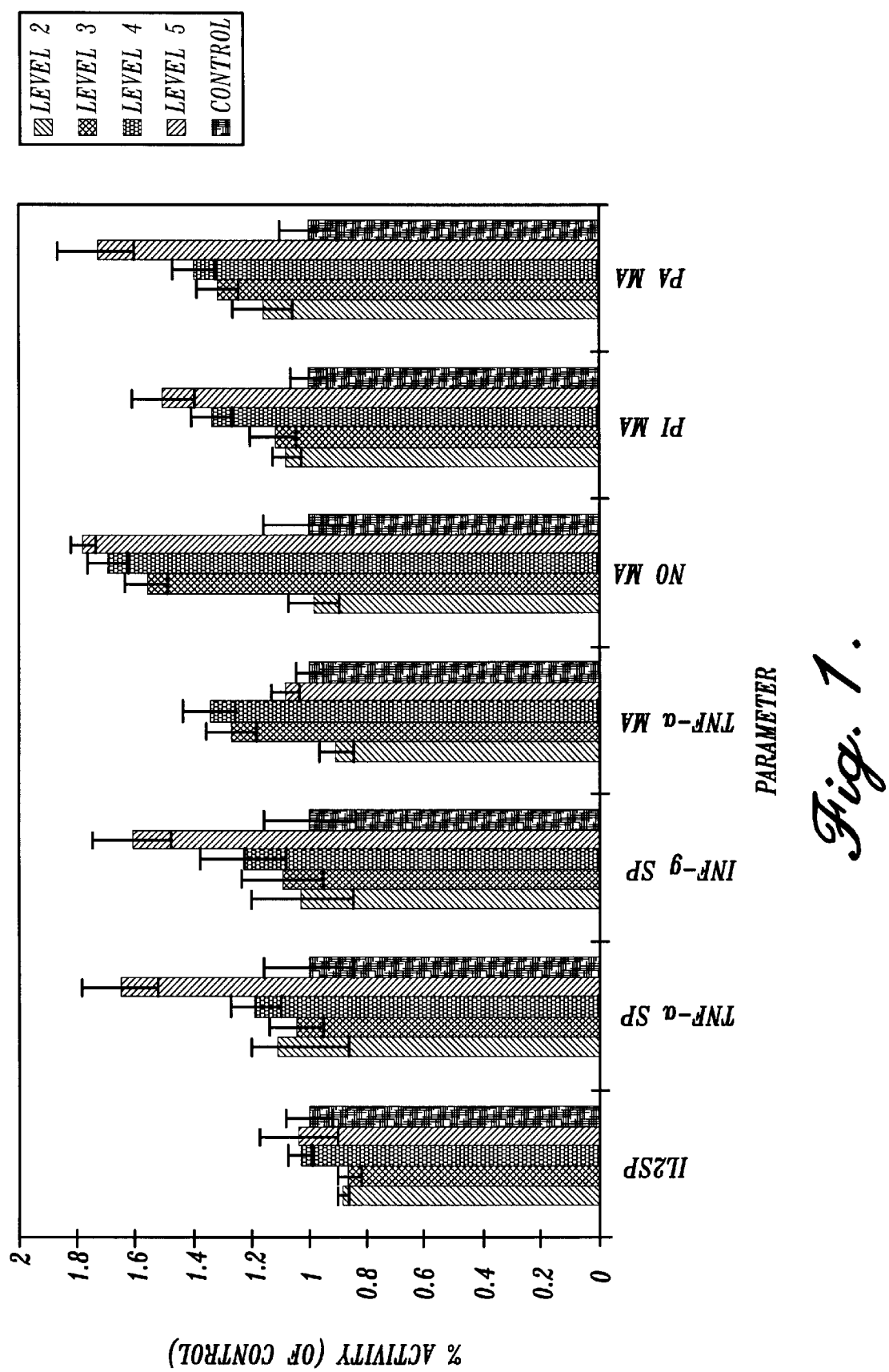
FIG. 1 shows the effect of different dosages of an Echinacea composition of the invention on various immune system parameters in rat. The Echinacea composition includes Echinacea cichoric acid, alkylamide and polysaccharide extracts as set forth in Example 8 herein. The dosage levels are set forth in Table 1 herein. Abbreviations are: IL2 SP: interleukin-2 production in splenocytes; TNF-α SP: tumor necrosis factor alpha production in splenocytes; TNF-γ SP: interferon gamma production in splenocytes; TNF-α MA: tumor necrosis factor alpha in alveolar macrophages; NO MA: nitric oxide production in alveolar macrophages; PI MA: phagocytic index in alveolar macrophages; PA MA: phagocytic activity in alveolar macrophages. Results are normalized to control values.

Echinacea can be propagated from seed, crown division and by planting root sections, preferably 10–12 cm in length. The seeds can be sown outdoors immediately after ripening in the autumn and germinate the following spring, but the rate of emergence is affected by the degree of seed dormancy, which varies with species. Seed germination is affected by several factors. Long-term seed storage at room temperature for three years or more will reduce germination rate. Seed size and inflorescence position do not affect seed germination, however seeds harvested at physiological maturity, but prior to senescence, have a higher germination rate than seeds harvested after desiccation. In the experience of the present inventors, seed source (i.e., the seed supplier) accounts for the majority of variation of E. purpurea germination rate. In particular, the presence of Echinacea hybrid seeds in commercially-purchased batches of seed is undesirable. A presently preferred method of identifying Echinacea hybrid seeds is as follows. The seeds to be tested are germinated in planters with daily watering. Seedlings are allowed to grow for one week after germination. The seedlings are then removed and washed thoroughly with water and dried. The clean seedlings are next processed with a kitchen blender until they are finely blended. The plant material is removed by filtering through 5 µm filters. The remaining liquid is concentrated by evaporation under vacuum to half of its original volume and then filtered through a 0.45 µm filter for HPLC analysis. HPLC analysis, using the cichoric acid assay method described in Example 6 herein, will show a distinct cichoric acid peak for non-hybridized seeds, whereas the cichoric acid peak is missing in hybridized seeds.

Seedling emergence from directly-seeded fields may not be as uniform as germinating indoors after stratification. One presently preferred method for seed stratification is to mix seeds with clean sand (in a ratio of 1:1, v/v) in a plastic bag and maintain moisture at about ten percent throughout a four to six week period at a temperature of from about 1° C. to about −4° C. The stratified seeds are then separated from the sand and can be sown on the soil surface or 0.5 cm deep in flats or small pots filled with a mixture of peat and perlite, (in a ratio of 1:1, v/v). Seeds planted in flats maintained at about 18–20° C. typically start to emerge within seven to ten days after planting. Seedlings are preferably grown in a green house or indoors with supplementary light until transplanting to the outdoors. Typically there are about 257,000 seeds/kg for E. purpurea and up to about 319,000 seeds/kg for E. angustifolia. About 500 g of seed is required to provide transplants for a 0.5 hectare (ha) field.

Asexual propagation through cuttings and cell cultures is also possible. Asexual propagation can produce a large population of genetically identical plants which can be improved through selective breeding or genetic engineering for higher yields of active compounds.

In the wild, Echinacea typically grows in poor, rocky soil under full sun light. However, it also thrives under cultivation in moderately rich and well-drained loam or sandy loam soil, which is neutral to slightly acid (pH 6–7). Echinacea is a root crop, rocky or heavy soil should therefore be avoided. Although Echinacea is drought tolerant, water is important for its growth, and regular irrigation is recommended.

Intensive fertilization produces a high herb yield but low root yield. A balanced fertilizer, low in nitrogen and including an adequate amount of phosphorus and potassium, is usually sufficient. Bone meal or phosphatic rock (14.5–20 kg/ha) and wood ash (45–51.5 kg/ha) applied before sowing, and cow or horse manure applied in 3 applications after planting, is a presently preferred combination of organic fertilizer for growing Echinacea. Fish fertilizer (including N—$P_2O_5$—$K_2O$ in a ratio of 5-2-2, respectively) applied at a working concentration of 4 mL/L promotes the growth of E. purpurea. Besides manure and decomposed municipal waste, a green cover crop such as quinoa, stinging nettle or red clover is also beneficial. Chemical fertilizer can also be used for non-organic cultivation. Nitrogen fertilizer is used for general plant health and more specifically, for producing a leafy, dark green plant. Phosphate fertilizers will increase flowering.

Additionally, plant spacing affects yield. Preferably, Echinacea should be planted 30 cm apart in 120 cm wide beds, allowing five rows per bed and giving approximately 74,000 plants/ha. This is a maximum density that may be too dense if a vigorous Echinacea species is used, or if the plants are grown for longer than four years.

Mulch serves the purpose of maintaining soil moisture and temperature, and more importantly controls weeds. Seedlings thrive under black plastic mulch or bark mulch. If seeding outdoors, a mulch of clean straw (2–3 cm) over the seed is considered essential. Echinacea is not tolerant of weeds, thus weed control is an important factor. In the experience of the present inventors, with respect to organically grown Echinacea, black plastic or bark mulch is the best weed control measure, especially for newly established plants. Plastic mulch can decrease the labor cost for weed control by seventy to eighty percent. Bark mulching should be done immediately after planting and should be coarse (i.e., utilizing pieces of bark mulch having dimensions of greater than about 2 cm by 2 cm) to enable the surface to dry out and create conditions unfavorable for weed germination. Land preparation, at least one year before planting, is another way to get rid of perennial weeds and reduce the annual weed population. A preferred method of land preparation is to turn the soil over in Spring when the weeds have grown up, but before planting the Echinacea plants. In this way, the weeds are destroyed by exposing their roots.

Thorough soil cultivation is essential to optimize growth and yield of Echinacea. Normally the roots do not reach desirable size until 3–4 years after sowing. With carefully regulated growing conditions, the yield from *E. angustifolia* can reach up to 2.5 tons/ha. Yields for *E. purpurea* are typically higher than that for *E. angustifolia*.

The Echinacea compositions of the present invention include standardized amounts of at least two Echinacea components. More preferably the Echinacea compositions of the present invention include standardized amounts of at least three Echinacea components. In this context the term "standardized amount", or grammatical equivalents thereof, means a desired, quantified amount of an Echinacea component. It is desirable to formulate Echinacea compositions to contain standardized amounts of Echinacea components because such standardized, Echinacea compositions provide the consumer with a consistent (i.e., does not vary between batches),effective dose of the biologically active component (s).

Presently preferred Echinacea extracts useful for preparing the Echinacea compositions of the present invention are enriched in at least one Echinacea component that is capable of inducing a biological response, such as stimulation of immune function, when introduced into a living organism. By way of non-limiting example, Echinacea components useful for preparing the Echinacea compositions of the present invention include: essential oils, alkamides (including alkylamides), cichoric acid, polysaccharides, polyalkynes and polyalkenes. Representative examples of Echinacea essential oils include, borneol, bornylacetate, pentadeca-8-en-2-one, germacrene D, caryophyllene, caryophyllene epoxide and palmitic acid. Echinacea essential oils are described, for example, in A. Awang and D. Kindack, *Canadian Pharmaceutical Journal* 124: 512–516 (1991), incorporated herein by reference, and in Bauer, R., "Echinacea Species as Potential Immunostimulatory Drugs", Economic and Medicinal Plant Research, vol. 5, p. 261–267 (1991). Presently preferred Echinacea components useful for preparing the Echinacea compositions of the present invention are cichoric acid (most preferably cichoric acid prepared in accordance with the present invention), Echinacea alkylamides (most preferably Echinacea alkylamides prepared in accordance with the present invention) and Echinacea polysaccharides (most preferably Echinacea polysaccharides prepared in accordance with the present invention).

In one presently preferred embodiment, the present invention provides Echinacea compositions including a standardized amount of a first Echinacea component and a standardized amount of a second Echinacea component, wherein the first and second Echinacea components are each independently selected from the group consisting of cichoric acid (most preferably cichoric acid prepared in accordance with the present invention), Echinacea alkylamides (most preferably Echinacea alkylamides prepared in accordance with the present invention) and Echinacea polysaccharides (most preferably Echinacea polysaccharides prepared in accordance with the present invention), and wherein the standardized amount of cichoric acid is from about 0.2 mg/ml to about 500 mg/ml, more preferably from about 0.3 mg/ml to about 30 mg/ml, most preferably from about 5 mg/ml to about 30 mg/ml; the standardized amount of Echinacea alkylamides is from about 0.02 mg/ml to about 50 mg/ml, more preferably from about 0.05 mg/ml to about 50 mg/ml, most preferably from about 0.8 mg/ml to about 50 mg/ml; and the standardized amount of Echinacea polysaccharides is from about 10 mg/ml to about 800 mg/ml. more preferably from about 20 mg/ml to about 800 mg/ml, most preferably from about 50 mg/ml to about 800 mg/ml.

In a second presently preferred embodiment, the present invention provides Echinacea compositions including a standardized amount of cichoric acid (most preferably cichoric acid prepared in accordance with the present invention), Echinacea alkylamides (most preferably Echinacea alkylamides prepared in accordance with the present invention) and Echinacea polysaccharides (most preferably Echinacea polysaccharides prepared in accordance with the present invention), and wherein the standardized amount of cichoric acid is from about 0.2 mg/ml to about 500 mg/ml, more preferably from about 0.3 mg/ml to about 30 mg/ml, most preferably from about 5 mg/ml to about 30 mg/ml; the standardized amount of Echinacea alkylamides is from about 0.02 mg/ml to about 50 mg/ml, more preferably from about 0.05 mg/ml to about 50 mg/ml, most preferably from about 0.8 mg/ml to about 50 mg/ml; and the standardized amount of Echinacea polysaccharides is from about 10 mg/ml to about 800 mg/ml, more preferably from about 20 mg/ml to about 800 mg/ml, most preferably from about 50 mg/ml to about 800 mg/ml.

In a third presently preferred embodiment, the present invention provides Echinacea compositions including a standardized amount of a first Echinacea component and a standardized amount of a second Echinacea component, wherein the first and second Echinacea components are each independently selected from the group consisting of cichoric acid (most preferably cichoric acid prepared in accordance with the present invention), Echinacea alkylamides (most preferably Echinacea alkylamides prepared in accordance with the present invention) and Echinacea polysaccharides (most preferably Echinacea polysaccharides prepared in accordance with the present invention), and wherein the standardized amount of cichoric acid is from about 0.01 mg/g to about 500 mg/g, more preferably from about 0.05 mg/g to about 500 mg/g, most preferably from about 15 mg/g to about 500 mg/g; the standardized amount of Echinacea alkylamides is from about 0.005 mg/g to about 100 mg/g, more preferably from about 0.1 mg/g to about 100 mg/g, most preferably from about 5 mg/g to about 100 mg/g; and the standardized amount of Echinacea polysaccharides is from about 5 mg/g to about 900 mg/g, more preferably from about 10 mg/g to about 900 mg/g, most preferably from about 200 mg/g to about 900 mg/g.

In a fourth presently preferred embodiment, the present invention provides Echinacea compositions including a standardized amount of cichoric acid (most preferably cichoric acid prepared in accordance with the present invention), Echinacea alkylamides (most preferably Echinacea alkylamides prepared in accordance with the present invention) and Echinacea polysaccharides (most preferably Echinacea polysaccharides prepared in accordance with the present invention)., and wherein the standardized amount of cichoric acid is from about 0.01 mg/g to about 500 mg/g, more preferably from about 0.05 mg/g to about 500 mg/g, most preferably from about 15 mg/g to about 500 mg/g; the standardized amount of Echinacea alkylamides is from about 0.005 mg/g to about 100 mg/g, more preferably from about 0.1 mg/g to about 100 mg/g, most preferably from about 5 mg/g to about 100 mg/g; and the standardized amount of Echinacea polysaccharides is from about 5 mg/g to about 900 mg/g, more preferably from about 10 mg/g to about 900 mg/g, most preferably from about 200 mg/g to about 900 mg/g.

In another aspect, the present invention provides methods for preparing Echinacea compositions, the methods including the step of combining amounts of at least two Echinacea components, preferably three Echinacea components, sufficient to yield an Echinacea composition including standardized amounts of each of the combined Echinacea components. In this context the term "standardized amount", or grammatical equivalents thereof, means a desired, quantified amount of an Echinacea component. Presently preferred Echinacea components useful for preparing Echinacea compositions, in accordance with the present invention, are capable of inducing a biological response, such as stimulation of immune function, when introduced into a living organism. By way of non-limiting example, Echinacea components useful for preparing Echinacea compositions, in accordance with the methods of the present invention, include: essential oils, alkamides (including alkylamides), cichoric acid, polysaccharides, polyalkynes and polyalkenes. Presently preferred Echinacea components useful for preparing Echinacea compositions, in accordance with the methods of the present invention, are cichoric acid (most preferably cichoric acid prepared in accordance with the present invention), Echinacea alkylamides (most preferably Echinacea alkylamides prepared in accordance with the present invention) and Echinacea polysaccharides (most preferably Echinacea polysaccharides prepared in accordance with the present invention). The Echinacea compositions prepared in accordance with the present invention can be in liquid form, gel form or solid form, such as a powder or capsules, and are preferably adapted for administration (more preferably oral administration) to a human being.

In one presently preferred embodiment, the present invention provides methods for preparing Echinacea compositions including the step of combining an amount of a first Echinacea component and an amount of a second Echinacea component, each of said first and second Echinacea components being independently selected from the group consisting of cichoric acid (most preferably cichoric acid prepared in accordance with the present invention), Echinacea alkylamides (most preferably Echinacea alkylamides prepared in accordance with the present invention) and Echinacea polysaccharides (most preferably Echinacea polysaccharides prepared in accordance with the present invention), said amount of cichoric acid being an amount sufficient to yield an Echinacea composition including a cichoric acid standardized amount of from about 0.2 mg/ml to about 500 mg/ml, more preferably from about 0.3 mg/ml to about 30 mg/ml, most preferably from about 5 mg/ml to about 30 mg/ml; said amount of Echinacea alkylamides being an amount sufficient to yield an Echinacea composition including an alkylamides standardized amount of from about 0.02 mg/ml to about 50 mg/ml, more preferably from about 0.05 mg/ml to about 50 mg/ml, most preferably from about 0.8 mg/ml to about 50 mg/ml; and said amount of Echinacea polysaccharides being an amount sufficient to yield an Echinacea composition including an Echinacea polysaccharides standardized amount of from about 10 mg/ml to about 800 mg/ml, more preferably from about 20 mg/ml to about 800 mg/ml, most preferably from about 50 mg/ml to about 800 mg/ml.

In a second presently preferred embodiment, the present invention provides methods for preparing Echinacea compositions including the step of combining an amount of cichoric acid (most preferably cichoric acid prepared in accordance with the present invention), an amount of Echinacea alkylamides (most preferably Echinacea alkylamides prepared in accordance with the present invention) and an amount of Echinacea polysaccharides (most preferably Echinacea polysaccharides prepared in accordance with the present invention), said amount of cichoric acid being an amount sufficient to yield an Echinacea composition including a cichoric acid standardized amount of from about 0.2 mg/ml to about 500 mg/ml, more preferably from about 0.3 mg/ml to about 30 mg/ml, most preferably from about 5 mg/ml to about 30 mg/ml; said amount of Echinacea alkylamides being an amount sufficient to yield an Echinacea composition including an alkylamides standardized amount of from about 0.02 mg/ml to about 50 mg/ml, more preferably from about 0.05 mg/ml to about 50 mg/ml, most preferably from about 0.8 mg/ml to about 50 mg/ml; and said amount of Echinacea polysaccharides being an amount sufficient to yield an Echinacea composition including an Echinacea polysaccharides standardized amount of from about 10 mg/ml to about 800 mg/ml, more preferably from about 20 mg/ml to about 800 mg/ml, most preferably from about 50 mg/ml to about 800 mg/ml.

In a third presently preferred embodiment, the present invention provides methods for preparing Echinacea compositions including the step of combining an amount of a first Echinacea component and an amount of a second Echinacea component, each of said first and second Echinacea extracts being independently selected from the group consisting of cichoric acid (most preferably cichoric acid prepared in accordance with the present invention), Echinacea alkylamides (most preferably Echinacea alkylamides prepared in accordance with the present invention) and Echinacea polysaccharides (most preferably Echinacea polysaccharides prepared in accordance with the present invention), said amount of cichoric acid being an amount sufficient to yield an Echinacea composition including a cichoric acid standardized amount of from about 0.01 mg/g to about 500 mg/g, more preferably from about 0.05 mg/g to about 500 mg/g, most preferably from about 15 mg/g to about 500 mg/g; said amount of Echinacea alkylamides being an amount sufficient to yield an Echinacea composition including an alkylamides standardized amount of from about 0.005 mg/g to about 100 mg/g, more preferably from about 0.1 mg/g to about 100 mg/g, most preferably from about 5 mg/g to about 100 mg/g; and said amount of Echinacea polysaccharides being an amount sufficient to yield an Echinacea composition including an Echinacea polysaccharides standardized amount of from about 5 mg/g to about 900 mg/g, more preferably from about 10 mg/g to about 900 mg/g, most preferably from about 200 mg/g to about 900 mg/g.

In a fourth presently preferred embodiment, the present invention provides methods for preparing Echinacea compositions including the step of combining an amount of cichoric acid (most preferably cichoric acid prepared in accordance with the present invention), an amount of Echinacea alkylamides (most preferably Echinacea alkylamides prepared in accordance with the present invention) and an amount of Echinacea polysaccharides (most preferably Echinacea polysaccharides prepared in accordance with the present invention), said amount of cichoric acid being an amount sufficient to yield an Echinacea composition including a cichoric acid standardized amount of from about 0.01 mg/g to about 500 mg/g, more preferably from about 0.05 mg/g to about 500 mg/g, most preferably from about 15 mg/g to about 500 mg/g; said amount of Echinacea alkylamides being an amount sufficient to yield an Echinacea composition including an alkylamides standardized amount of from about 0.005 mg/g to about 100 mg/g, more preferably from about 0.1 mg/g to about 100 mg/g, most preferably from about 5 mg/g to about 100 mg/g; and said amount of Echinacea polysaccharides being an amount sufficient to yield an Echinacea composition including an Echinacea polysaccharides standardized amount of from about 5 mg/g to about 900 mg/g, more preferably from about 10 mg/g to about 900 mg/g, most preferably from about 200 mg/g to about 900 mg/g.

Echinacea compositions prepared in accordance with the present invention can be in liquid form, gel form or solid form, such as a powder or capsules, and are preferably adapted to be administered (more preferably orally administered) to a human being. Typically, prior to blending to form Echinacea compositions of the present invention, aliquots of Echinacea extracts are tested for potency. Extracts are adjusted to the desired concentration(s) by concentration or dilution with appropriate fillers or solvents (including water, alcohol, soy oil or other oils, lecithin, glycerin, and so on). Vessels for blending can be purged with nitrogen gas and the blending can be carried out under nitrogen to prevent oxidation. The Echinacea compositions, or the individual Echinacea extracts, can be formulated in an alcohol or glycerin base. Powdered Echinacea extracts or compositions can be manufactured through spray-drying or freeze-drying. Liquid Echinacea extracts or compositions can also be microencapsulated into a free-flowing powder form. Liquid Echinacea compositions or extracts can be used directly as ingredients in soft-gelatin liquid capsules and hard-gelatin capsules, and tablets can be made from the powdered material.

In general, the Echinacea extracts and compositions prepared in accordance with the present invention can include one or more excipients. Suitable pharmaceutically acceptable excipients include processing agents and drug delivery modifiers and enhancers, such as, for example, vegetable oil powder, croscarmellose sodium, acacia gum and guar gum. Other suitable pharmaceutically acceptable excipients are described in "Remington's Pharmaceutical Sciences," Mack Pub. Co., New Jersey (1991), incorporated herein by reference.

In another aspect, the present invention provides methods for preparing enriched Echinacea extracts. The presently preferred Echinacea extracts of the invention are enriched in Echinacea alkylamides, Echinacea polysaccharides or cichoric acid. The methods of the present invention include the steps of selecting an Echinacea plant at a developmental stage having an enhanced amount of a desired component (such as Echinacea alkylamides, Echinacea polysaccharides or cichoric acid); selecting a portion of the plant that is enriched in the desired component, and contacting the selected portion with an amount of a solvent, selected from the group consisting of ethanol and water, effective to extract the desired component from the plant portion. Preferably the Echinacea extract is then concentrated. Any species of Echinacea plant can be utilized in the practice of the present invention, but the presently preferred species is *E. purpurea*. Presently preferred components extracted from Echinacea plants, in accordance with the present invention, are polysaccharides, alkylamides and cichoric acid. When the methods of the present invention are used to extract polysaccharides, the extracted Echinacea plants are preferably from about one to about four years old. Preferably polysaccharides are extracted from the flowers, leaves, stems and/or roots of Echinacea plants. When the methods of the present invention are used to extract alkylamides, the extracted Echinacea plants are preferably from about two to about four years old. Preferably alkylamides are extracted from mature flowers and roots of Echinacea plants. When the methods of the present invention are used to extract cichoric acid, the extracted Echinacea plants are preferably from about one to about three years old. Preferably cichoric acid is extracted from young Echinacea plants, from leaves of Echinacea plants, and from immature flowers. Extraction of Echinacea plant material utilizes a ratio (by weight) of plant material to solvent of no more than about two parts plant material to about one part solvent. The presently preferred ratio (by weight) of plant material to solvent is about one part plant material to about four parts solvent.

In accordance with one aspect of the present invention, polysaccharides may be extracted from selected Echinacea plant material by contacting the plant material with a mixture of ethanol and water containing from about 0.1% ethanol to about 50% ethanol (w/w), preferably from about 5% ethanol to about 20% ethanol. Polysaccharides are preferably extracted from the flowers, leaves, stems and/or roots of Echinacea plants. The aerial parts of the plant typically contain higher concentrations of polysaccharides than the roots, and mature flowers typically contain higher concentrations than immature flowers. The preferred extraction temperature for extracting polysaccharides is from about 20° C. to about 80° C., more preferably from about 30° C. to about 70° C., most preferably from about 30° C. to about 50° C. The duration of polysaccharide extraction is preferably from about 48 hours to about 14 days, more preferably from about three days to about twelve days, most preferably from about four days to about eight days. Extended extraction times at elevated temperatures ensure that polysaccharides are extracted as completely as possible, although some hydrolysis of polysaccharides occurs at higher temperatures, but cold temperatures slow the extraction process significantly. Polysaccharide extracts containing low concentrations of ethanol must be monitored closely to prevent bacterial, yeast, or fungal growth and consequent spoilage.

Polysaccharide extracts prepared in accordance with the present invention typically contain polysaccharide at a concentration of from about 0.5 mg/mL to about 20.0 mg/mL. In the practice of the present invention, polysaccharide extracts are preferably concentrated to a final polysaccharide concentration of from about 1 mg/mL to about 900 mg/mL, more preferably to a polysaccharide concentration of from about 60 mg/mL to about 900 mg/mL, most preferably to a polysaccharide concentration of from about 100 mg/mL to about 900 mg/mL. The presently preferred method for concentrating polysaccharide extracts is evaporation. Evaporation is preferably performed at a temperature of from about 20° C. to about 85° C. for a period of from about 5 hours to about 6 days. The vacuum applied is typically from about 5 millibars (mbar) to about 320 mbar absolute vacuum.

In accordance with one aspect of the present invention, alkylamides may be extracted from selected Echinacea plant material by contacting the plant material with a mixture of ethanol and water containing from about 50% ethanol to about 95% ethanol (w/w), preferably from about 65% ethanol to about 85% ethanol, more preferably from about 70% ethanol to about 80% ethanol. Alkylamides are found in all Echinacea species and the total alkylamide concentration (and the complexity of the alkylamide fraction) is greater in roots than in leaves. Isobutylamides are the major component of the alkylamide fraction in the roots of *E angustifolia* and *E. purpurea*, although they are a minor component of the alkylamide fraction in the roots of *E pallida*. Isobutylamides are present in the aerial parts of *E. angustifolia, E. purpurea* and *E. pallida*. Mature flowers and roots of Echinacea plants are preferably used as starting materials to prepare alkylamide extracts since these plant materials have the highest amount of alkylamides. Alkylamides are preferably extracted from Echinacea plants that are greater than about two years old.

The preferred extraction temperature for extracting Echinacea alkylamides is from about 4° C. to about 85° C., more preferably from about 30° C. to about 70° C., most preferably from about 40° C. to about 60° C. The duration of alkylamide extraction is preferably from about 24 hours to about 7 days, more preferably from about one day to about four days, most preferably from about two days to about three days. The chosen alkylamide extraction temperature depends, in part, on the content of other compounds in the starting, raw plant material. In the case of plant material that contains a large proportion of alkylamides and little cichoric acid, extractions can be carried out at 85° C.; however, when a significant amount of cichoric acid is also present in the starting plant material, and it is desirable to preserve the cichoric acid in the final extract, the extraction temperature should be lowered to less than 40° C. to avoid degradation of the chicoric acid.

Alkylamide extracts prepared in accordance with the present invention typically contain alkylamides at a concentration of from about 0.1 mg/mL to about 3.0 mg/mL. In the practice of the present invention, alkylamide extracts are preferably concentrated to a final alkylamide concentration of from about 0.1 mg/mL to about 300 mg/mL, more preferably to an alkylamide concentration of from about 1 mg/mL to about 300 mg/mL, most preferably to an alkylamide concentration of from about 20 mg/mL to about 300 mg/mL. The presently preferred method for concentrating alkylamide extracts is evaporation. Evaporation is typically performed at a temperature of from about 10° C. to about 90° C. for a period of from about 3 hours to about 3 days. The vacuum applied is typically from about 5 millibars (mbar) to about 320 mbar absolute vacuum.

In accordance with the present invention, cichoric acid may be extracted from selected Echinacea plant material by contacting the plant material with a mixture of ethanol and water containing from about 40% ethanol (w/w) to about 95% ethanol (w/w), preferably from about 40% ethanol (w/w) to about 85% ethanol (w/w), more preferably from about 50% ethanol (w/w) to about 70% ethanol (w/w). The parts of the Echinacea plant containing the highest concentrations of cichoric acid are preferably extracted in order to yield extracts having a high concentration of cichoric acid. In *E. purpurea*, the highest concentrations of cichoric acid are found in the roots, flowers and leaves, whereas in *E. angustifolia* cichoric acid is only found in the roots. In general, cichoric acid is preferably extracted from young plants, leaves, and immature flowers. In this aspect of the invention, Echinacea plants are selected that are preferably less than one year old.

The preferred extraction temperature for extracting cichoric acid is from about 4° C. to about 45° C., more preferably from about 4° C. to about 30° C. The duration of cichoric acid extraction is preferably from about 24 hours to about 3 days, more preferably from about 24 hours to about 40 hours, most preferably from about 24 hours to about 36 hours. Cichoric acid degradation becomes significant at extraction temperatures higher than about 40° C. As much as 95% of the cichoric acid initially present in the plant material can be lost if the extraction is carried out at greater than 40° C. for more than 48 hours. More extended extractions can give extracts completely devoid of cichoric acid. Cichoric acid extracts prepared in accordance with the present invention typically contain cichoric acid at a concentration of from about 0.2 mg/mL to about 2.0 mg/mL. In the practice of the present invention, cichoric acid extracts are preferably concentrated to a final cichoric acid concentration of from about 1 mg/mL to about 700 mg/mL, more preferably to a cichoric acid concentration of from about 5 mg/mL to about 700 mg/mL, most preferably to a cichoric acid concentration of from about 30 mg/mL to about 700 mg/mL. The presently preferred method for concentrating cichoric acid extracts is evaporation. Evaporation is preferably performed at a temperature of from about 10° C. to about 45° C. for a period of from about 5 hours to about 2.5 days. The vacuum applied is typically from about 5 millibars (mbar) to about 320 mbar absolute vacuum.

In the methods of the present invention for preparing Echinacea extracts, the Echinacea extraction conditions preferably minimize degradation of polysaccharides, alkylamides and cichoric acid. Many biologically active compounds in Echinacea are sensitive to degradation and each compound or compound group is sensitive to different conditions which may cause degradation. For example, cichoric acid is not stable in solution. Degradation of cichoric acid can occur quickly by phenol oxidase-mediated oxidation, by hydrolysis, and by chemical degradation. Heat can also cause degradation of cichoric acid. Similarly, endogenous plant enzymes (such as glycoside hydrolases and amylases) can degrade polysaccharides by hydrolysis. In addition, polysaccharide extracts are easily spoiled by mold, yeast, and fungal growth. Alkylamides degrade quickly once dried or purified.

One method of reducing degradation of biologically active compounds during extraction is to utilize an atmosphere rich in nitrogen or argon, thereby excluding oxygen. Nitrogen can be applied by thoroughly purging all equipment and containers before any liquid transfer. Further, nitrogen gas can be bubbled continuously through Echinacea liquid extracts during storage and extraction. Strict control of process parameters, such as temperature and concentration, can also help to reduce oxidation and hydrolysis. For example, enzymatic hydrolysis of polysaccharides into monosaccharide residues occurs much more readily at 74° C. than at 40° C. Chemical hydrolysis occurs at 75° C. to 120° C. By maintaining lower temperatures during processing, hydrolysis can be minimized. Oxidation is also reduced by lower processing temperatures. A further aid in decreasing endogenous enzymatic activity is to concentrate the liquid extracts to minimize the water content.

Since many consumers demand that herb-derived products are produced with only non-toxic solvents, many solvents routinely used in the laboratory such as hexane, chloroform, ethers, and ketones are preferably not used in the practice of the present invention. The methods of the present invention for preparing Echinacea extracts utilize water and ethanol as extraction solvents, and different ethanol and water mixtures are utilized for extracting different active ingredients from Echinacea plants. Preferably, plant material is extracted in liquid solvent at a ratio (by weight) of one part plant material to four parts liquid solvent. However, extracts can also be made utilizing a plant material to liquid solvent ratio of as high as 2 parts plant material to one part liquid solvent. Echinacea extracts have also been prepared in accordance with the present invention by utilizing a plant material to liquid solvent ratio of one part plant material to twenty parts liquid solvent. Extractions with a high solvent to plant material ratio result in the extraction of a greater amount of active compounds from the plant in a more dilute form. The dilute extracts are preferably concentrated to reach the desired concentrations of polysaccharides, alkylamides and/or cichoric acid.

Alternatively, supercritical carbon dioxide can be used as a non-toxic solvent to extract biologically active components from Echinacea plants. Supercritical fluid is circulated through the plant material until the extraction has occurred as completely as desired. Echinacea extracts prepared using supercritical fluid carbon dioxide contain mostly non-polar compounds (such as oils). Various additional extraction solvents (such as propane and acetone) can be added to supercritical fluid carbon dioxide in order to extract a higher proportion of polar compounds, but only he addition of water and ethanol is acceptable to the health-conscious consumer.

In general, extraction vessels utilized in the methods of the present invention for preparing Echinacea extracts are large containers with one or more openings through which plant materials and extraction solvents can be easily loaded and removed. An agitation mechanism can be built into the extraction vessel so that extraction occurs with constant agitation to reduce extraction time. Extraction vessels as small as 500 mL and as large as 3000 L have been successfully utilized in the practice of the present invention. Vessels should be constructed from materials resistant to degradation by ethanol, preferably polypropylene and stainless steel.

In the practice of the methods of the present invention for preparing Echinacea extracts, Echinacea extracts are preferably concentrated in order to reduce storage space, to increase storage stability (i.e., by reducing the amount of water), and to achieve desired concentrations of polysaccharides, alkylamides and cichoric acid. The concentration step is preferably optimized to minimize the loss of biological activity of the polysaccharides, alkylamides and cichoric acid. Since high temperatures cause rapid degradation of many compounds, concentration is usually performed at low temperatures and under reduced pressure. Usually a rotary evaporator is used. Evaporation reaction flasks typically range in size from between 20 L and 100 L. Between 5–90% of the solvent used for the extracts can be recovered.

In yet another aspect, the present invention provides liquid Echinacea extracts enriched in one or more member of the group consisting of Echinacea polysaccharides, Echinacea alkylamides and cichoric acid. Presently preferred Echinacea extracts enriched in polysaccharides include polysaccharides at a concentration greater than about 1% (w/v), more preferably greater than about 5% (w/v), most preferably greater than about 10% (w/v). Presently preferred Echinacea extracts enriched in alkylamides include alkylamides at a concentration greater than about 0.1% (w/v), more preferably greater than about 1.0% (w/v), most preferably greater than about 3.0% (w/v). Presently preferred Echinacea extracts enriched in cichoric acid include cichoric acid at a concentration greater than about 0.2% (w/v), more preferably greater than about 0.5% (w/v), most preferably greater than about 3.0% (w/v).

In yet another aspect, the present invention provides solid Echinacea extracts enriched in one or more member of the group consisting of Echinacea polysaccharides, Echinacea alkylamides and cichoric acid. Presently preferred Echinacea extracts enriched in polysaccharides include polysaccharides at a concentration greater than about 0.01% (w/w), more preferably greater than about 0.05% (w/w), most preferably greater than about 20% (w/w). Presently preferred Echinacea extracts enriched in alkylamides include alkylamides at a concentration greater than about 0.001% (w/w), more preferably greater than about 0.01% (w/w), most preferably greater than about 0.5% (w/w). Presently preferred Echinacea extracts enriched in cichoric acid include cichoric acid at a concentration greater than about 0.005% (w/w), more preferably greater than about 0.05% (w/w), most preferably greater than about 1.5% (w/w).

A presently preferred Echinacea polysaccharide extract of the present invention includes at least 60% (by weight) arabinose and galactose, and the polysaccharide molecules have a molecular weight greater than about 10,000.

A presently preferred Echinacea alkylamide extract of the present invention includes greater than about 70% (w/w) isobutylamides. A presently more preferred Echinacea alkylamide extract of the present invention has an isobutylamide concentration of greater than about 70% (w/w) and includes greater than about 30% (w/w) 2E, 4E, 8E, 10E/Z tetraene-dodeca-isobutylamide.

In yet another embodiment, the present invention provides nutritional compositions formulated to provide a standardized dose of at least two, preferably three, Echinacea components. The presently preferred Echinacea components are cichoric acid, Echinacea polysaccharides and Echinacea alkylamides. The presently preferred, standardized dose of Echinacea alkylamides is from about 0.01 mg to about 100 mg, more preferably from about 0.01 mg to about 40 mg, most preferably from about 0.1 mg to about 1 mg; the presently preferred, standardized dose of cichoric acid is from about 0.1 mg to about 120 mg, more preferably from about 0.1 mg to about 15 mg, most preferably from about 0.5 mg to about 3 mg; the presently preferred, standardized dose of Echinacea polysaccharides is from about 1 mg to about 500 mg, more preferably from about 5 mg to about 100 mg, most preferably from about 10 mg to about 50 mg.

In yet another aspect, the present invention provides methods for enhancing immune system activity in a mammal. The methods comprise administering to a mammal an effective daily dosage of an Echinacea composition comprising standardized amounts of Echinacea cichoric acid, Echinacea alkylamides and Echinacea polysaccharides. Representative standardized amounts of Echinacea cichoric acid are from 5 $\mu$g/Kg body weight to 2000 $\mu$g/Kg body weight, such as from 120 $\mu$g/Kg body weight to 1000 $\mu$g/Kg body weight (e.g., 800 $\mu$g/Kg body weight). Representative standardized amounts of Echinacea alkylamides are from 0.5 $\mu$g/Kg body weight to 200 $\mu$g/Kg body weight, such as from 12 $\mu$g/Kg body weight to 100 $\mu$g/Kg body weight (e.g, 80 $\mu$g/Kg body weight). Representative standardized amounts of Echinacea polysaccharides are from 125 $\mu$g/Kg body weight to 50 mg/Kg body weight, such as from 3 mg/Kg body weight to 30 mg/Kg body weight (e.g., 20 mg/Kg body weight). By way of non-limiting example, the methods (that utilize Echinacea compositions as described above) for enhancing immune system activity in a mammal are useful for enhancing macrophage phagocytic activity, enhancing nitric oxide production by macrophages, enhancing TNF-$\alpha$ production by macrophages, enhancing IFN-$\gamma$ production by splenocytes, and enhancing TNF-$\alpha$ production by splenocytes.

In a further aspect, the present invention provides methods for enhancing immune system activity in a mammal comprising administering to the mammal an effective daily dosage of an Echinacea extract selected from the group consisting of Echinacea alkylamides and Echinacea polysaccharides. Representative effective daily dosages of Echinacea alkylamides are from 0.5 µg/Kg body weight to 200 µg/Kg body weight, such as from 12 µg/Kg body weight to 100 µg/Kg body weight (e.g., 80 µg/Kg body weight). In accordance with this aspect of the invention, an effective daily dosage of Echinacea polysaccharides is useful for enhancing macrophage phagocytic activity, enhancing nitric oxide production by macrophages, and/or enhancing TNF-α production by macrophages.

Representative effective daily dosages of Echinacea polysaccharides are from 125 µg/Kg body weight to 50 mg/Kg body weight, such as from 3 mg/Kg body weight to 30 mg/Kg body weight (e.g., 20 mg/Kg body weight). In accordance with this aspect of the invention, an effective daily dosage of Echinacea polysaccharides is useful for enhancing TNF-α production by macrophages.

The following examples merely illustrate the best mode now contemplated for practicing the invention, but should not be construed to limit the invention.

EXAMPLE 1

Extraction of Alkylamides from Echinacea Plants

Echinacea plants are grown about two feet apart and watered once per week until one week before the flowers are harvested. Preferably the flowers of two and/or three year old *Echinacea purpurea* plants are harvested. Fully mature *Echinacea purpurea* flower cones are preferably collected in late August, and approximately 700 kg of flowers are typically collected from a one-acre field.

500 kg of freshly harvested flowers are macerated with a hammer mill to particles sizes of about 1.5 cm$^3$, or smaller, and then extracted with about 2000 kg of 75% ethanol for 72 hours at 35° C. Lower ethanol concentrations and temperatures reduce yield while higher ethanol concentrations and temperatures increase cost. The liquid and plant material are agitated at 3 revolutions per minute with rotating mechanical paddles spaced approximately 20 cm apart and radiating from a center axle in the extraction vessel. At the end of the extraction period, 2300 kg of the liquid extract is removed from the extracted flowers.

The liquid extract now contains about 0.6 mg/mL of alkylamides. Concentration of the liquid extract at 25 mbar and 40° C. for 30 hours yields about 100 kg of alkylamide-rich liquid concentrate having an alkylamide concentration of about 10 mg/mL. The concentrate is characterized by a dark-green color, because of the presence of plant chlorophyll, and typically contains less than about 1 mg/mL of cichoric acid and less than about 10 mg/mL of polysaccharides.

EXAMPLE 2

Extraction of Cichoric Acid from Echinacea Plants

The seedlings are germinated from selected, non-hybridized seeds in late February and early March and transplanted to fields by middle or late March. Plants are spaced about two feet apart and watered twice weekly until harvest. Black plastic mulch is used to reduce growth of weeds and to speed up plant growth. The seeds are carefully selected since contamination with *Echinacea angustifolia* seeds (or seeds from *E. angustifolia/E. purpurea* hybrids) will reduce the yield of cichoric acid more than 20-fold because of increased enzymatic degradation. The plants are harvested as whole plants in late September, and the stem, leaves and flowers of the plants are removed for extraction. Typically, one acre of *Echinacea purpurea* plants yields approximately 1000 kg of plant material. Preferably, one year old *Echinacea purpurea* plants are harvested.

500 kg of the freshly harvested plants are macerated with a hammer mill to produce particle sizes of about 1.5 cm$^2$ to about 4 cm$^2$. The macerated material is extracted with 2000 kg of 50% ethanol for 30 hours at 25° C. Lower ethanol concentration and higher extraction temperature allow for increased degradation while higher ethanol concentration and lower temperatures reduce yield. Nitrogen gas is continuously purged through the extraction liquid to reduce the amount of cichoric acid degradation. The extraction liquid is circulated through the plant mash by a rotary pump with a capacity of up to 500 L per hour. At the end of the extraction period, 2100 kg of liquid extract having a cichoric acid concentration of about 2.0 mg/ml can be obtained.

Concentration of the liquid extract at 10 mbar and 35° C. for 20 hours yields 100 kg of cichoric acid rich concentrate having a cichoric acid concentration of 30 mg/mL. The concentrate is characterized by a dark-green color, resulting from the presence of plant chlorophyll, and contains less than 2 mg/mL of alkylamides and less than 20 mg/mL of polysaccharides.

EXAMPLE 3

Extraction of Polysaccharides from Echinacea Plants

Plants are grown about two feet apart and watered once a week until one week before the harvest. Fully mature *Echinacea purpurea* flower cones are collected in late August. Typically, approximately 700 kg of flowers are collected from a one-acre field of *Echinacea purpurea* plants. Preferably, two and/or three year old *Echinacea purpurea* plants are harvested.

500 kg of freshly harvested flowers are macerated with a hammer mill to particle sizes of about 1.5 cm$^3$, or smaller, and then extracted with 2000 kg of 20% ethanol for 72 hours at 55° C. Higher ethanol concentrations and lower temperatures reduce yield while lower ethanol concentrations increase microbial load of the finished extract, and higher temperatures increase cost. The liquid and plant material are agitated at 3 revolutions per minute with rotating mechanical paddles, spaced approximately 20 cm apart, radiating from a center axle in the extraction vessel. At the end of the extraction period, 1900 kg of the liquid extract is removed from the extracted flowers.

The liquid extract now typically contains about 15 mg/mL of polysaccharides, which can be concentrated at 50 mbar, 60° C. for 15 hours to yield about 200 kg of concentrate having a polysaccharide concentration of about 120 mg/mL. The concentrate is characterized by a dark brown color and typically contains less than about 2 mg/mL of alkylamides and less than about 2 mg/mL of cichoric acid.

EXAMPLE 4

Assay of Polysaccharides Extracted from Echinacea Plants

The polysaccharide assay method is a modified version of the method set forth in AOAC Official Methods of Analysis (1995), AOAC Official Method 988.12, "Dextran in Raw Cane Sugar", 44.1.30, "Part E—Phenol-H$_2$SO$_4$ Test." The polysaccharide assay can be performed in 13×100 mm disposable culture tubes. The final reaction volume of the assay is 1.5 ml. Distilled water is added to the polysaccharide sample to yield a water plus polysaccharide sample volume of 400 μl. 100 μl of a 5% (w/v), reagent-grade phenol solution is then added to the diluted polysaccharide sample and mixed. One milliliter of concentrated sulphuric acid (reagent grade, 95–98% concentrated) is then added and quickly mixed by vortexing. The tubes containing the samples are then placed in a boiling water bath for two minutes. The tubes are then allowed to cool at room temperature for 30 minutes and the absorbency of the samples at 485 nanometers (nm) are measured against a distilled water blank using a spectrophotometer. The spectrophotometer should be able to accurately read $A_{485}$ absorbance values over the range of 0 to 1.5.

An Echinacea polysaccharides concentration standard is prepared from a water extraction of Echinacea flowers, with ethanol precipitations in the following manner. Concentrated Echinacea polysaccharide material is obtained as described in Example 3 herein. The extract is further concentrated to about 400 mg/mL of polysaccharides. This concentrate is then precipitated with 4 volumes of 95% ethanol at 4° C. overnight. The precipitate is removed with centrifugation and redissolved in 35–40° C. water bath. The material that does not dissolve at this stage is discarded and the supernatant is precipitated with one volume of 30% (w/v) of trichloroacetic acid. Precipitate is again removed with centrifugation and the supernatant is precipitated with four more volumes of ethanol. The precipitated polysaccharides are dissolved in 2% sodium acetate solutions and precipitated a third time with ethanol. The supernatant is discarded and the precipitate is dissolved in water for dialysis with Spectra/Por ®10,000 MW cut-off dialysis tubing. Dialysis is carried out over three days and the remaining material is lyophilized to yield a fluffy solid material.

A known weight of the lyophilized polysaccharide is dissolved in a known volume of water to yield an Echinacea polysaccharides standard of known concentration. Dilutions of the Echinacea polysaccharides standard solution are made and the $A_{485}$ of each dilution measured in order to construct a standard curve of absorbance at 485 nanometers versus polysaccharide concentration.

EXAMPLE 5

Assay of Alkylamides Extracted from Echinacea Plants

The presently preferred alkylamides assay method is a modification of the method published by Bauer in *Planta Meidca*, 55, 367–371 (1989). The mobile phase of the method was changed from acetonitrile to methanol due to sample precipitation problems. The method uses an HPLC (high performance liquid chromatography) consisting of a gradient pump, an autosampler, and a UV-Visible detector. Preferably, a Hewlett Packard 1100 series HPLC system and a Hewlett Packard 1050 series HPLC system are used. A C-18 column, preferably a 125×4.0 mm Hypersil ODS column, with a matching 4.0 mm ×4.0 mm guard column, is used. The mobile phase consists of 60% methanol and 40% water (v/v) at the start of the analysis, and changes in a linear fashion to 95% methanol and 5% water at 12.5 minutes into the analysis. Total run time is 19.00 minutes with 4 minutes of post-run equilibration. The mobile phase is pumped at 1.00 mL/minute. 10 μL samples are injected and the sample absorbance at 254 nm is measured. Alkylamides elute the column at 2.0 minutes to 9.0 minutes. More specifically, dodeca-2E, 4E, 8E, 10E/Z-tetraenoic acid isobutylamide elutes at 5.0 to 8.0 minutes.

An alkylamide concentration standard is preferably prepared by extracting 500 ml of alkylamide-rich liquid concentrate, prepared as described in Example 3 herein, with 500 ml of petroleum ether at room temperature. The petroleum ether fraction is removed after one day and evaporated to dryness under vacuum and a dark, black, oily residue results. The residue is dissolved in a minimum of methanol (about 20 mL) and centrifuged to removed precipitates. Octadecyl-functionalized silica is set up in a glass column. A mobile phase consisting of 70% methanol and 30% water by volume is used for elution. Material prepared from the liquid concentrate is applied to the column and 10 mL fractions are collected. The fractions are analyzed for alkylamide content using the analysis method described and fractions containing 90% and higher purity of the alkylamide of interest are pooled. The pooled fractions are then rotor-evaporated at 45° C. to reduce total volume. Purified alkylamide fractions from column elution are evaporated to a clear (yellow colored) liquid under vacuum. Petroleum ether is added to the residue and warmed in a hot water bath. The residue and liquid is sonicated to saturate the solution with the purified alkylamide. The saturated solution is collected and allowed to cool to room temperature. The solution is then moved to –20° C. freezer. The crystals form overnight. 500 mL of saturated solution yields about 0.1–5 g of purified crystals, depending on the solubility of the specific alkylamide.

The purified alkylamide standard is dissolved at various concentrations and passed through an HPLC column as described herein. A calibration curve is constructed from the resulting peak areas versus concentrations of the alkylamide standard solutions. Peak areas from alkylamide samples of unknown concentration are compared against the calibration curve to determine the concentration in each sample.

EXAMPLE 6

Assay of Cichoric Acid Extracted from Echinacea Plants

The cichoric acid analysis method is a modification of the method published by Bauer in Planta Meidca, 57, 447–449 (1991). The mobile phase of the method was changed from acetonitrile to methanol due to sample precipitation problems. The method uses an HPLC (high performance liquid chromatography) consisting of a gradient pump, an autosampler, and a UV-Visible detector. In this case, a Hewlett Packard 1100 series HPLC system and a Hewlett Packard 1050 series HPLC system are used. A C-18 column, in this case a 125×4.0 mm Hypersil ODS column, with a matching 4.0 mm×4.0 mm guard column, is used. The mobile phase consists of 7.0% methanol and 93.0% water with 0.1% phosphoric acid (v/v) at the start of the analysis and changes in a linear fashion to 32% methanol and 68% water with 0.1% phosphoric acid (v/v) at 11.6 minutes into the analysis, which then changes to 40.7% methanol and 59.3% water with 0.1% phosphoric acid at 19.1 minutes. Total run time is 22.00 minutes with 3.50 minutes of post-run equilibration. The mobile phase is pumped at 1.00 ml/minute. 10 μl samples are injected and the data is collected at 330 nm. The peak area of the sample is compared against a purified chemical standard for quantitation. Caffeic acid derivatives elute the column at 7.0 minutes to 18.0 minutes. More specifically, cichoric acid elutes at 14.5 to 17.0 minutes.

A cichoric acid concentration standard is prepared in the following manner. Cichoric acid-rich liquid concentrate, prepared as described in Example 2 herein, is further reduced in volume by vacuum distillation at 50° C. The polysaccharides are removed with isopropanol precipitation using 2 parts isopropanol and 1 part distilled concentrate. The supernatant is removed and isopropanol is evaporated through vacuum distillation at 37° C. Distilled water at two times the volume of the concentrate is added and the pH of the concentrate is adjusted to pH 0–1 with concentrated hydrochloric acid. Cichoric acid is further purified by elution through a lipophilic Sephadex LH-20 column with 100% methanol as mobile phase. Fractions with cichoric acid purity of greater than 90%, as analyzed by the method described above, are pooled. The pooled fractions are reduced to dryness under vacuum and then redissolved in minimum amount of boiling hot water. Cichoric acid crystallizes out as short, white needles upon cooling.

The purified cichoric acid standard is dissolved at various concentrations and passed through an HPLC column as described herein. A calibration curve is constructed from the resulting peak areas versus concentrations of the cichoric acid standard solutions. Peak areas from cichoric acid samples of unknown concentration are compared against the calibration curve to determine the concentration in each sample.

EXAMPLE 7

Exemplary Echinacea Compositions of the Present Invention

By way of representative example, blended, commercial Echinacea compositions of the present invention are prepared in the following manner. Alkylamide-rich concentrate (prepared in accordance with Example 1, herein), cichoric-acid-rich concentrate (prepared in accordance with Example 2, herein), and polysaccharide-rich concentrate (prepared in accordance with Example 3, herein) are combined in the following volume ratios: 0.4:0.2:0.4, respectively. The concentrates are blended with a motorized mixer to obtain a homogeneous product. In a presently preferred embodiment, this combined liquid concentrate contains 5.2 mg/mL of alkylamides, 7.2 mg/mL of cichoric acid, and 56 mg/mL of polysaccharides. This blended composition is used to prepare commercial Echinacea compositions as follows:

- (a) An alcohol-free, commercial liquid Echinacea composition is prepared by evaporating the blended, Echinacea composition further to remove ethanol, and then diluting the evaporated composition 10 times by adding 9 times the volume of 70% (w/w) glycerin. The resulting material is blended thoroughly for a product containing 0.52 mg/mL of alkylamides, 0.72 mg/mL of cichoric acid, and 5.6 mg/mL of polysaccharides.
- (b) A commercial, liquid Echinacea composition that contains alcohol is prepared by diluting the blended, Echinacea composition 10 times by adding 9 times the volume of 40% (w/w) ethanol. The resulting material is blended thoroughly for a product containing 0.52 mg/mL of alkylamides, 0.72 mg/mL of cichoric acid, and 5.6 mg/mL of polysaccharides.
- (c) Commercial, liquid, Echinacea soft-gelatin capsules are prepared by diluting the blended, Echinacea composition 10 times by adding 9 times the volume of a mixture of 30% lecithin and 70% soy oil. The resulting material is blended thoroughly and then encapsulated into soft-gelatin capsules at 1.0 mL per capsule for a product containing 0.52 mg/capsule of alkylamides, 0.72 mg/capsule of cichoric acid, and 5.6 mg/capsule of polysaccharides.
- (d) Freeze-dried, Echinacea powders are prepared by mixing the blended, Echinacea composition with 9 times its volume of water and then lyophilizing with 10% (w/w) tri-calcium phosphate as a carrier. A dried cake is obtained after 30 hours of lyophilization. A free-flowing powder is obtained, once the freeze-dried cakes are milled through a 100 $\mu$m cone mill, including 2.6 mg/g of alkylamides, 3.6 mg/g of cichoric acid, and 2.8 mg/g of polysaccharides.
- (e) Micro-encapsulated Echinacea powders are prepared by mixing the blended, Echinacea composition with 1% (v/v) of vitamin E for stability and then micro-encapsulating the mixture with a cellulose and wax coating at 50%-fill (w/w) with capsules averaging 100 $\mu$m in size. The micro-capsules appear as a free-flowing powder with a composition of 2.6 mg/g of alkylamides, 3.6 mg/g of cichoric acid, and 2.8 mg/g of polysaccharides.
- (f) Hard-gelatin Echinacea capsules are prepared by mixing the freeze-dried powder (described in section (d) of this example) or the micro-encapsulated powder (described in section (e) of this example) with five parts (by weight) of microcrystalline cellulose and 2% (w/w) of magnesium stearate. The resulting powder is encapsulated in 1000 mg capsules to provide 0.52 mg/capsule of alkylamides, 0.72 mg/capsule of cichoric acid, and 5.6 mg/capsule of polysaccharides.
- (g) Echinacea tablets are prepared by mixing the freeze-dried powder (described in section (d) of this example) or the micro-encapsulated powder (described in section (e) of this example) with three parts (by weight) of di-calcium phosphate, two parts (by weight) of microcrystalline cellulose and 3% (w/w) of magnesium stearate. The resulting powder is tablet-punched in 1000 mg tablets to provide 0.52 mg/tablet of alkylamides, 0.72 mg/tablet of cichoric acid, and 5.6 mg/tablet of polysaccharides.

EXAMPLE 8

Effects of Echinacea Compositions and Extracts of the Invention on Immune Function The data set forth in this example shows that Echinacea extracts and compositions of the invention stimulate various aspects of the rat immune system.

*Animal Maintenance* and Tissue Sampling. Young, adult, male Sprague-Dawley rats (about 240 g each) were acclimatized in the laboratory for one week before administering the test material. One-hundred microliters of the test material of various concentrations, as specified herein, were administered to each animal, through a gavage needle, two times a day for four days. Blood and tissue samples were removed from the animals on the fifth day for analysis. Each test group included eight animals whose test results were averaged.

Test Material

The control sample administered to the animals was a mixture of ethanol and water. One of the following test materials was administered to each animal (the dose levels, expressed as microgrammes ($\mu$g) test material per kilogram (kg) body weight of test animal, are set forth in Table 1): one of four dose levels of Echinacea alkylamide extract, one of four dose levels of Echinacea cichoric acid extract, one of four dose levels of Echinacea polysaccharides extract, or one of four dose levels of an Echinacea composition that includes Echinacea alkylamide, cichoric acid, and polysaccharides extracts.

The Echinacea composition contained the three extracts listed in Table 1 in the specified amounts for the daily dose.

For example, the level 1 daily dosage of the Echinacea composition provided 0.5 µg/kg alkylamide, 5.0 µg/kg cichoric acid and 125 µg/kg polysaccharides. The Echinacea composition was prepared by blending the three Echinacea purpurea extracts (alkylamides, cichoric acid and polysaccharides) which were prepared as described in Examples 1–3 herein.

TABLE 1

|  | Level 1 (µg/kg) | Level 2 (µg/kg) | Level 3 (µg/kg) | Level 4 (µg/kg) | Level 5 (µg/kg) |
| --- | --- | --- | --- | --- | --- |
| Alkylamide | .05 | .4 | 12 | 80 | 200 |
| Cichoric acid | .5 | 4 | 120 | 800 | 2000 |
| polysaccharides | 12.5 | 100 | 300 | 2000 | 5000 |

Processing of Blood

Blood was obtained from the test animals by cardiac puncture and saved in an EDTA vacutainer tube which was centrifuged at 3000 rpm for 10 minutes (min.) to separate the plasma. The plasma was stored in a capped plastic tube at −30° C. until use.

Preparation of splenocytes. Spleens from the animals were pressed through a nylon mesh in cold Krebs-Ringer-HEPES solution (KRH) supplemented with 0.5% bovine serum albumin (BSA) and collected in 50 mL tubes. The collected cells were then centrifuged at 4° C. for 10 min. at 2000 rpm and the supernatant was decanted. One milliliter of lysis buffer ACK (containing aluminum chloride and potassium) was added to the cells. The cells were then washed twice with 50 mL of KRH+BSA. Cells were then re-suspended in 1 mL CCM (Complete Culture Medium containing RPMI-1640 and 4% fetal calf serum. RPMI-1640 is a bicarbonate-based buffer system developed by Moore and Woods as disclosed in the Tissue Culture Association Manual, 3: 503–508 (1976)) with penicillin, streptomycin, amphotericin, glutamine, 2-mercaptoethanol and HEPES, each of which components were present at a concentration of 1% (v/v). Cells were diluted to $3.0$–$5.0 \times 10^6$/mL and activated with 20 µL Concanavalin A (ConA) (10 µg/mL) and incubated for 48 hours. After 48 hours, the cells were centrifuged and the supernatant was collected and frozen at 30° C. for cytokine and nitric oxide assays.

Preparation of Alveolar Macrophages

Alveolar macrophages were obtained by bronchoalveolar lavaging with 40 mL of phosphate buffered saline (PBS). The cells were centrifuged at 4° C. for 20 min at 2000 rpm and the supernatant was discarded. 1 mL ACK was then added and then washed three times with cold PBS. The cells were then suspended in 1 mL RPMI supplemented with 10% fetal calf serum. Cells were diluted to $5$–$10 \times 10^6$ cells/mL and 100 µL of the diluted cells were incubated for 2 hours at 37° C. in V-bottom microtiter plates. The supernatant was discarded and the microtiter plate was washed 3 times with PBS. 200 µL of LPS was added to activate the cells, and the cells were then incubated for 24 hours. Supernatant was collected after incubation and frozen at −30° C. for cytokine and nitric oxide assays.

Phagocytosis assay

Macrophages were incubated for 3 hours at 37° C. for adhesion. They were then washed 3 times with 10% RPMI and then latex beads were added at a concentration of $2.5 \times 10^6$ beads/ 200 µL. Cells were incubated for one more hour and washed 5 times with RPMI. The cells were stained and phagocytosis was determined by microscopic examination.

Nitric Oxide Assay a stock solution of 4 mM sodium nitrite was made and diluted to 1 mM with 4% CCM buffer just before use. The sodium nitrite stock solution was used at various concentrations to construct a linear calibration curve. Griess reagent was prepared by dissolving 0.5 g sulfanilamide and 6 mL 85% phosphoric acid in 100 mL of water and dissolving 0.05 g N-(1-naphthyl)ethyl-enediamine in 100 mL of water. Supernatants from macrophages or splenocytes were added to Griess reagent and allowed to stand for 10 minutes. Absorbance was measured at 540 nm and nitric oxide concentration was calculated from the sodium nitrite standard curve.

TNF-α, INF-γ, and Interleukin-2 Assays

Antibodies were obtained from any one of the following suppliers: Sigma Chemicals, Box 14508 St. Louis, Mo. 63178, U.S.A.; R&D Systems, or PharMagen, 6300 Kitimat Road, Unit 1, Mississauga, Ontario L5N 5M1, Canada. The assays were performed using a standard ELISA protocol.

Figure 2:
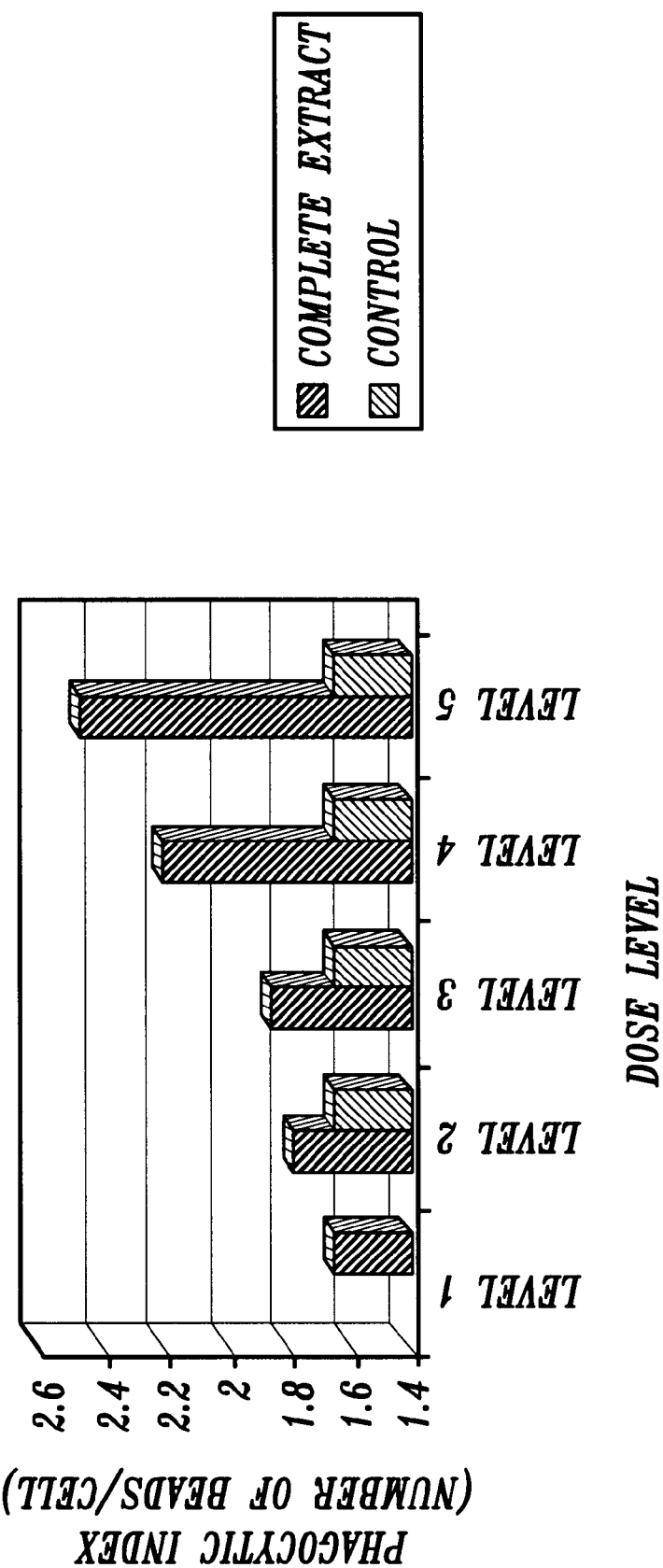
FIG. 2 shows the effect on the phagocytic index of rat alveolar macrophages of different dosages of an Echinacea composition of the invention. The Echinacea composition includes Echinacea cichoric acid, alkylamide and polysaccharide extracts as set forth in Example 8 herein. The dosage levels are set forth in Table 1 herein.

Effects of Echinacea Compositions and Extracts of the Invention on Phagocytic Activity and Phagocytic Index in Alveolar Macrophages as shown in FIG. 1, all dosage levels (levels 2–5 as set forth in Table 1) of the Echinacea composition described in this Example caused an increase in the phagocytic activity and the Phagocytic Index of alveolar macrophages. As shown more clearly in FIG. 2, as the dosage increased, so did the magnitude of the effect on phagocytic activity and the Phagocytic Index.

Figure 3:
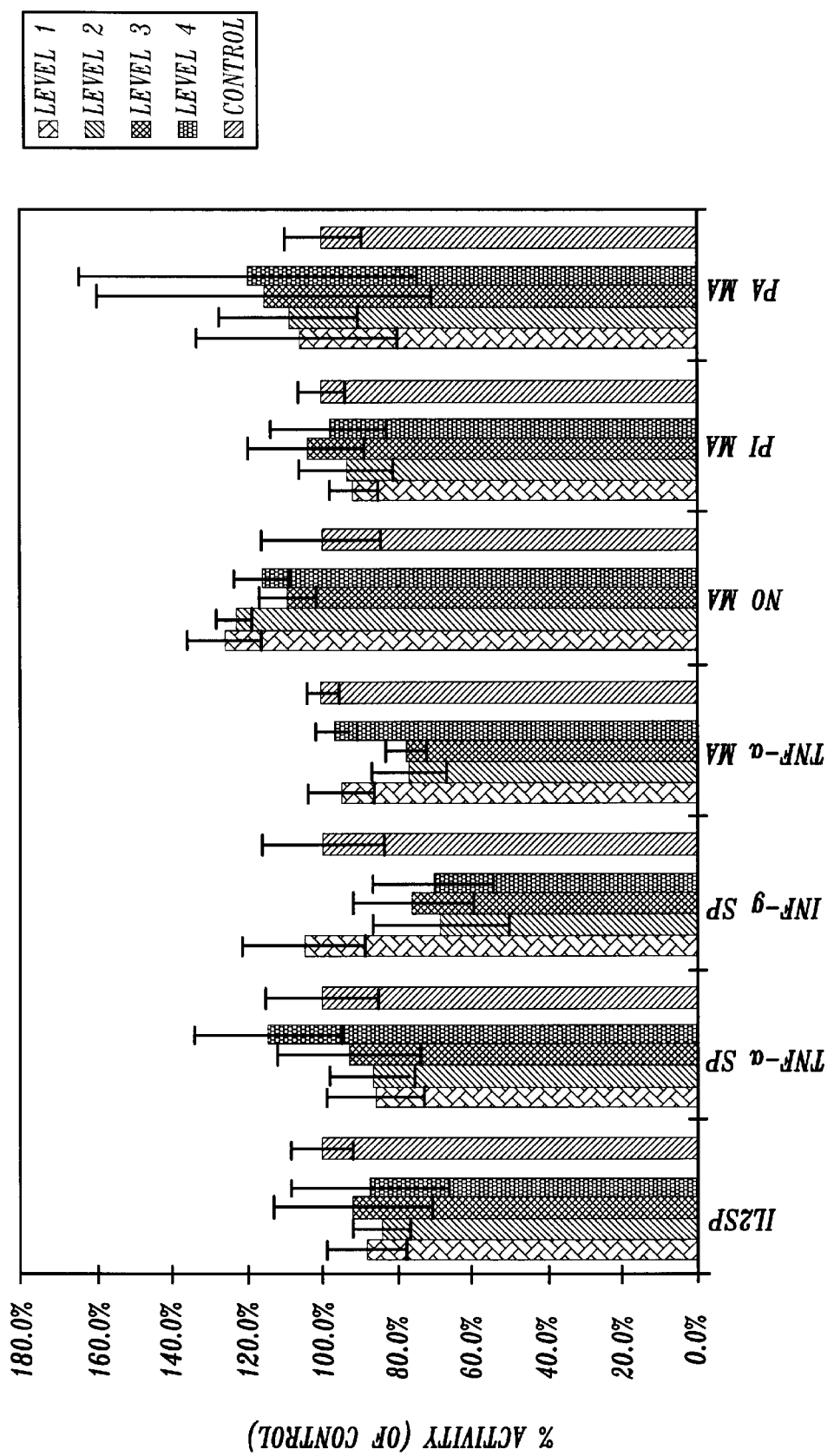
FIG. 3 shows the effect of an Echinacea cichoric acid extract of the invention on various immune system parameters in rat. The Echinacea cichoric acid extract was prepared as described in Example 2 herein. Abbreviations are: IL2 SP: interleukin-2 production in splenocytes; TNF-α SP: tumor necrosis factor alpha production in splenocytes; INF-γ SP: interferon gamma production in splenocytes; TNF-α MA: tumor necrosis factor alpha in alveolar macrophages; NO MA: nitric oxide production in alveolar macrophages; PI MA: phagocytic index in alveolar macrophages; PA MA: phagocytic activity in alveolar macrophages. Results are normalized to control values.

As shown in FIG. 3, an Echinacea cichoric acid extract of the invention, prepared as described in Example 2 herein and administered to rats at dosage levels 1–4 as set forth in Table 1, had no significant effect on the phagocytic activity or the phagocytic index of rat alveolar macrophages. Similarly, as shown in FIG. 4, an Echinacea polysaccharide extract of the invention, prepared as described in Example 3 herein and administered to rats at dosage levels 1–4 as set forth in Table 1, had no significant effect on the phagocytic activity or the phagocytic index of rat alveolar macrophages.

Figure 5:
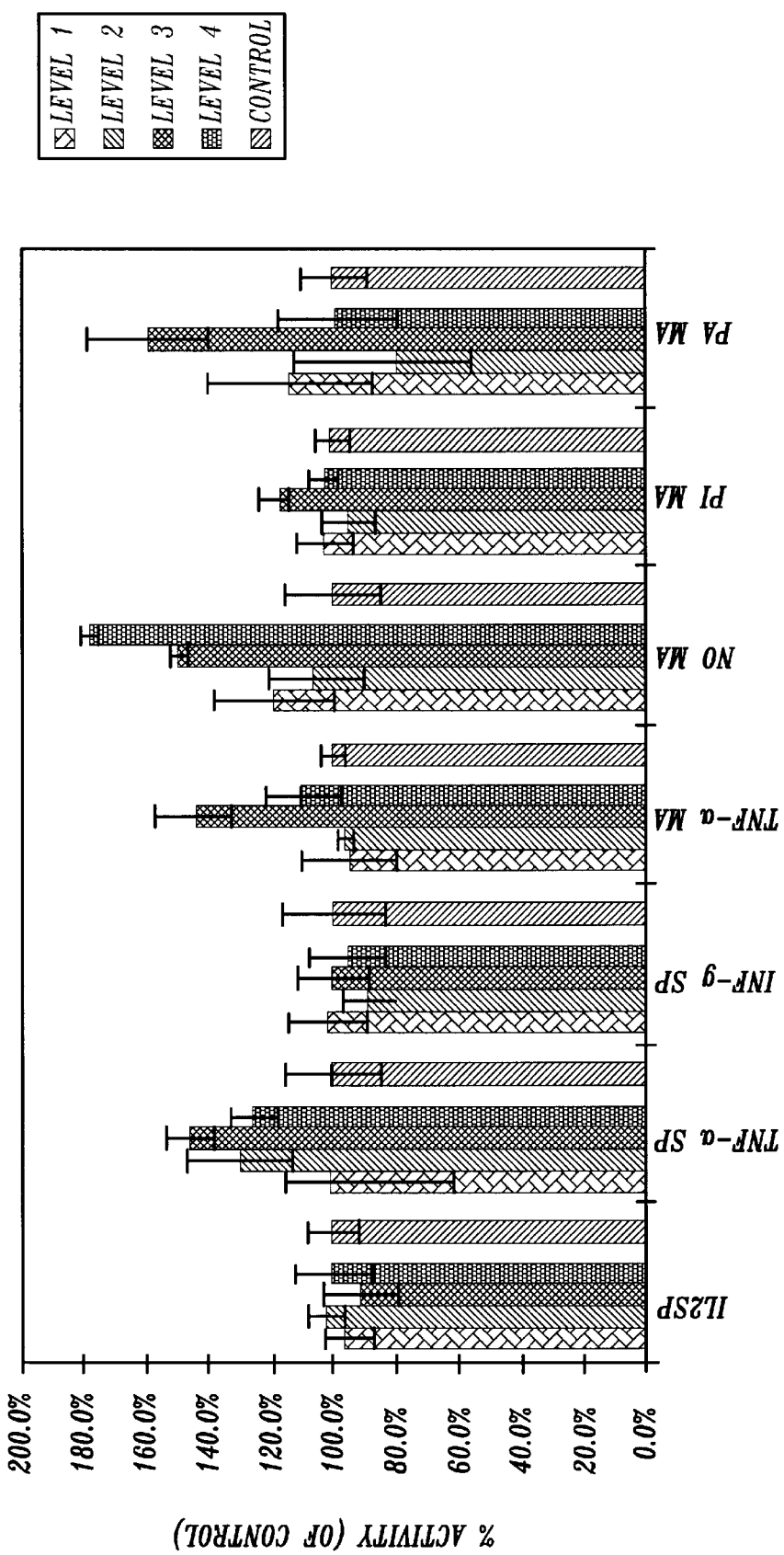
FIG. 5 shows the effect of an Echinacea alkylamide extract of the invention on various immune parameters in rat. The Echinacea alkylamide extract was prepared as described in Example 1 herein. Abbreviations are: IL2 SP: interleukin-2 production in splenocytes; TNF-α SP: tumor necrosis factor alpha production in splenocytes; INF-γ SP: interferon gamma production in splenocytes; TNF-α : MA: tumor necrosis factor alpha in alveolar macrophages; NO MA: nitric oxide production in alveolar macrophages; PI MA: phagocytic index in alveolar macrophages; PA MA: phagocytic activity in alveolar macrophages. Results are normalized to control values.
Figure 6:
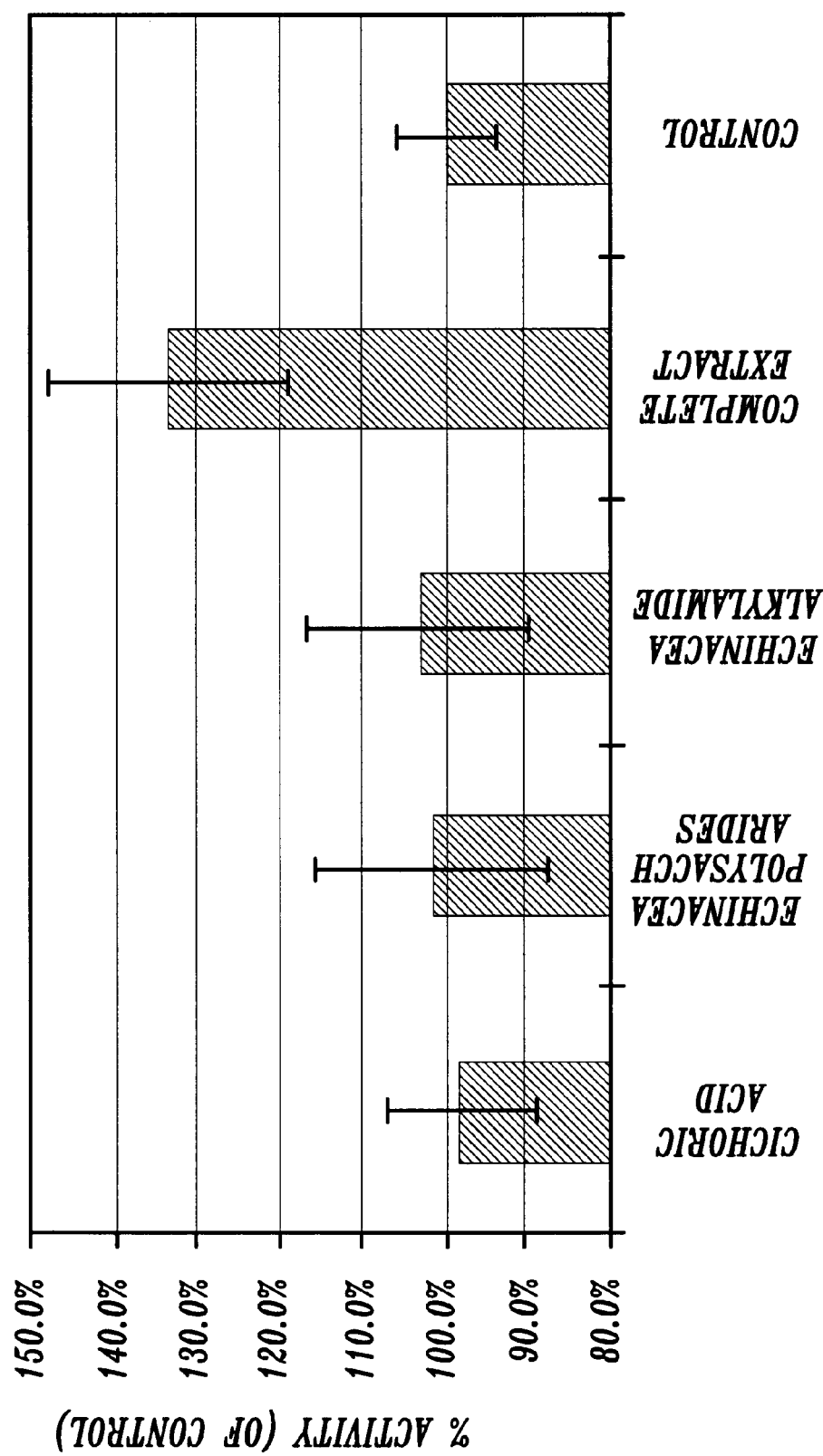
FIG. 6 shows the effect of an Echinacea composition of the invention, and the effect of each of its component cichoric acid, alkylamide and polysaccharide extracts, on the phagocytic index of rat alveolar macrophages. The Echinacea composition includes Echinacea cichoric acid, alkylamide and polysaccharide extracts as set forth in Example 8 herein. The dosage of the Echinacea composition was Level 4 as set forth in Table 1 herein, i.e., the Echinacea composition provided a daily dosage of Echinacea cichoric acid at 800 µg/kg, Echinacea polysaccharides at 20 mg/kg, and Echinacea alkylamides at 80 µg/kg. Echinacea cichoric acid was separately administered at a daily dosage of 800 µg/kg, Echinacea polysaccharides were separately administered at a daily dosage of 20 mg/kg, and Echinacea alkylamides were separately administered at a daily dosage of 80 µg/kg. A mixture of water and ethanol was administered to control rats.

In contrast, as shown in FIG. 5, an Echinacea alkylamides extract of the invention, prepared as described in Example 1 herein and administered to rats at dosage levels 1–4 as set forth in Table 1, enhanced both the phagocytic activity and the phagocytic index of rat alveolar macrophages compared to control rats treated with a mixture of ethanol and water. In particular, at dose level 3 the alkylamide extract significantly increased both the activity and the phagocytic index of the macrophages, with up to 60% increase in the activity and 50% increase in the index as compared to the controls. FIG. 6 shows a comparison of the effect on the phagocytic index of the Echinacea composition described in this Example, and the individual Echinacea cichoric acid, alkylamide and polysaccharide extracts. It is clear from FIG. 6 that the Echinacea composition showed a statistically significant synergistic activity compared to the individual compounds.

Effects of Echinacea Compositions and Extracts of the Invention on the Production of Nitric Oxide by Alveolar Macrophages as shown in FIG. 1, dosage levels 3–5, as set forth in Table 1, of the Echinacea composition described in this Example caused an increase in the production of nitric oxide by alveolar macrophages. As the dosage increased, so did the magnitude of the level of nitric oxide.

Figure 4:
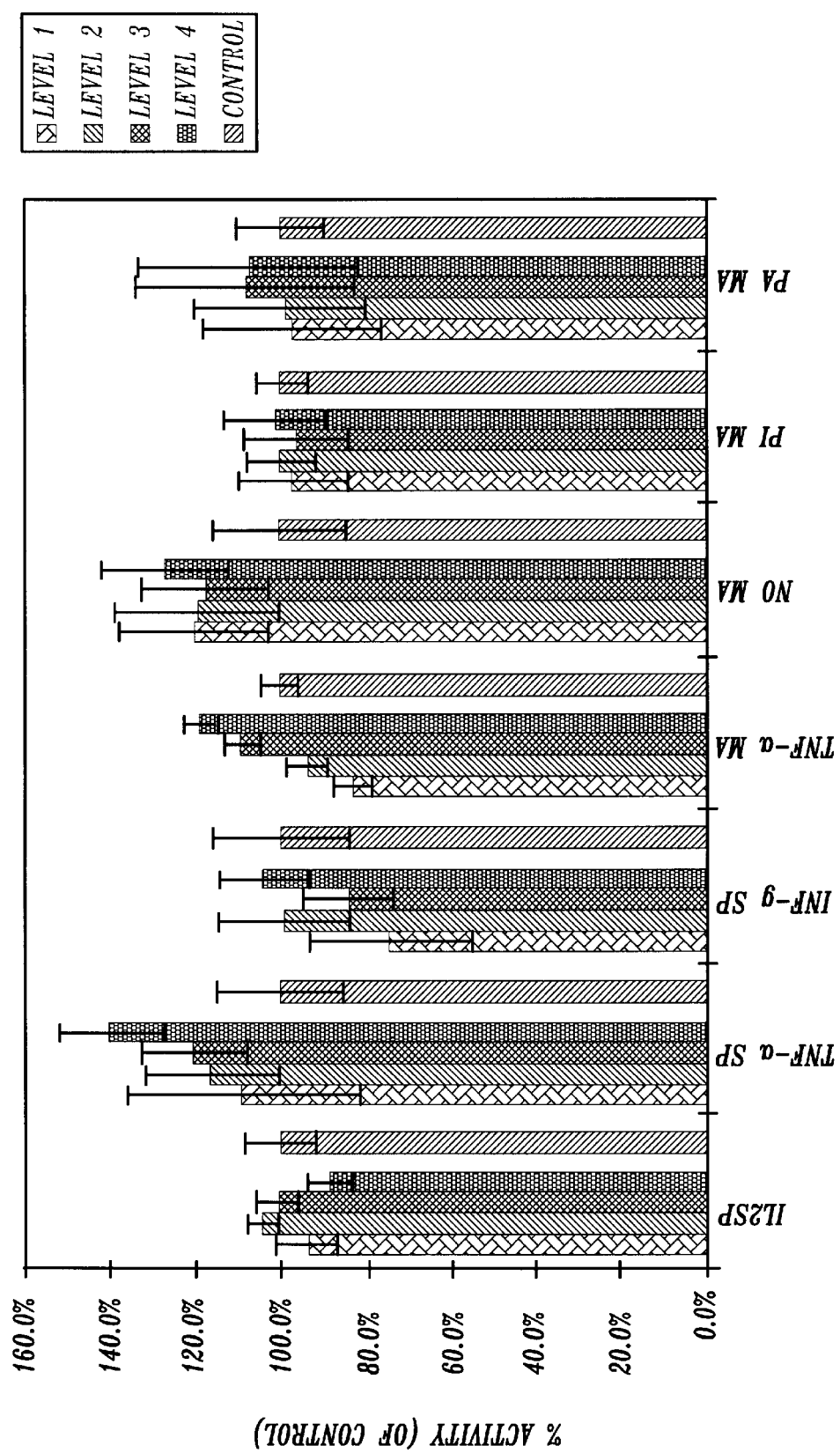
FIG. 4 shows the effect of an Echinacea polysaccharide extract of the invention on various immune parameters in rat. The Echinacea polysaccharide extract was prepared as described in Example 3 herein. Abbreviations are: IL2 SP: interleukin-2 production in splenocytes; TNF-α SP: tumor necrosis factor alpha production in splenocytes; INF-γ SP: interferon gamma production in splenocytes; TNF-α MA: tumor necrosis factor alpha in alveolar macrophages; NO MA: nitric oxide production in alveolar macrophages; PI MA: phagocytic index in alveolar macrophages; PA MA: phagocytic activity in alveolar macrophages. Results are normalized to control values.

As shown in FIGS. 3 and 4, Echinacea cichoric acid and polysaccharide extracts, prepared as described in Examples 2 and 3 herein, did not significantly increase the level of nitric oxide production by alveolar macrophages. In contrast, as shown in FIG. 5, dosage levels 1–4 (especially dosage levels 3 and 4) of an Echinacea alkylamides extract, prepared as described in Example 1 herein, caused a significant increase in the level of nitric oxide produced by alveolar macrophages.

Figure 7:
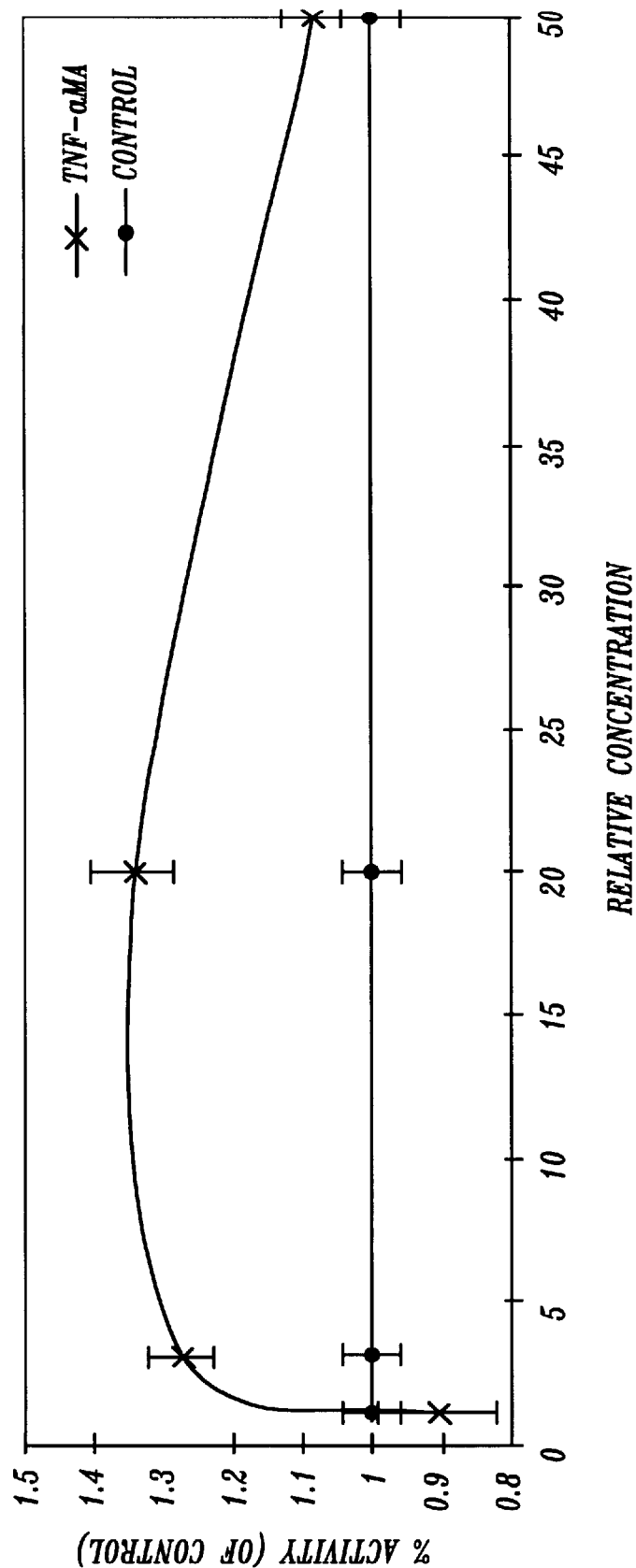
FIG. 7 shows the effect on TNF-α production in rat alveolar macrophages of different dosages of an Echinacea composition of the invention. The Echinacea composition includes Echinacea cichoric acid, alkylamide and polysaccharide extracts as set forth in Example 8 herein. TNF-α MA: tumor necrosis factor alpha in alveolar macrophages. Relative concentrations were obtained by normalizing each of the dose concentrations in Table 1 to the concentrations at dose level 2 set forth in Table 1.

Effects of Echinacea Compositions and Extracts of the Invention on the Production of TNF-α in Macrophages as shown in FIG. 1, the Echinacea composition described in this Example caused an increase in the production of TNF-α by alveolar macrophages in dosages up to level 4. Initially TNF-α production increases with increasing dosage of the Echinacea composition, then the response decreases. As shown in FIG. 7, the optimum Echinacea composition dosage occurs between Level 3 and Level 4.

As shown in FIG. 3, Echinacea cichoric acid extract, prepared as described in Example 2 herein, did not significantly increase the level of TNF-α production by alveolar macrophages. In contrast, as shown in FIGS. 4 and 5, Echinacea polysaccharide extract and Echinacea alkylamide extract, prepared as described in Examples 3 and 1 herein, both caused a significant increase in the level of TNF-α produced by alveolar macrophages. The stimulatory effect of the alkylamide extract was especially strong at dosage level 3. However at alkylamide dosage level 4, the production of TNF-α returned to that of controls. This might be a consequence of pronounced increase in nitric oxide production at this dose.

Effects of Echinacea Compositions and Extracts of the Invention on the Production of IFN-γ in Splenocytes as shown in FIG. 1, all dosage levels (levels 2–5 as set forth in Table 1) of the Echinacea composition described in this Example caused an increase in IFN-γ production by splenocytes. The effects were most pronounced at dosage levels 4 and 5.

As shown in FIGS. 3–5, the Echinacea cichoric acid, alkylamide and polysaccharide extracts did not cause a significant increase in IFN-γ production by the splenocytes.

Effects of Echinacea Compositions and Extracts of the Invention on the Production of TNF-α in Splenocytes as shown in FIG. 1, dosage level 5 of the Echinacea composition described in this Example caused a significant increase in TNF-α production by splenocytes.

Figure 8:
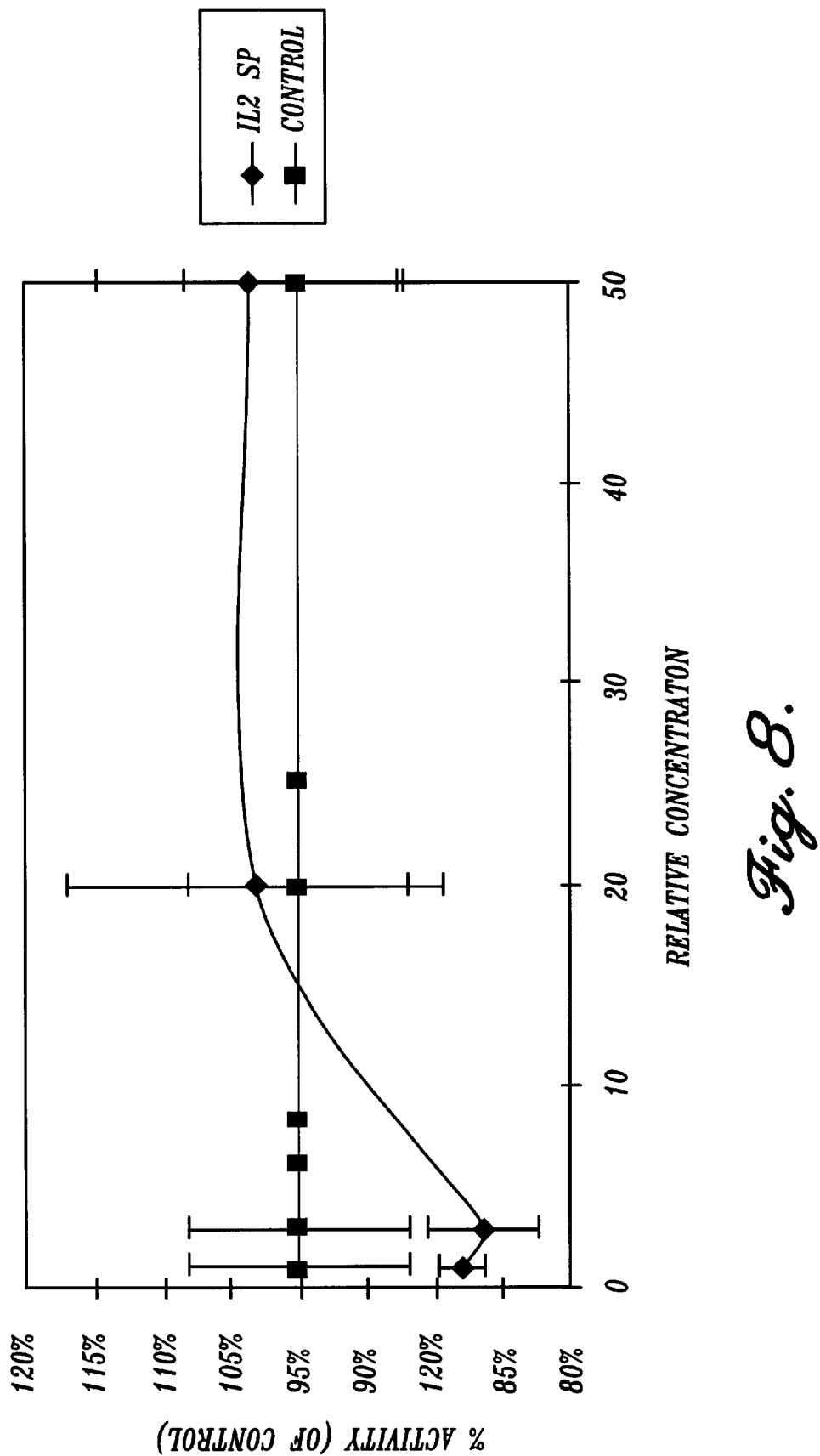
FIG. 8 shows the effect of different dosages of an Echinacea composition of the invention on rat splenocyte production of Interleukin-2. The Echinacea composition includes Echinacea cichoric acid, alkylamide and polysaccharide extracts as set forth in Example 8 herein. The Echinacea composition was administered at the dosage levels set forth in Table 1 herein. IL2 SP: Splenocyte production of interleukin-2. Results are normalized to the Control values. Relative concentrations were obtained by normalizing each of the dose concentrations in Table 1 to the concentrations at dose level 2 set forth in Table 1.

Effects of Echinacea Compositions and Extracts of the Invention on the Production of IL-2 in splenocytes as shown in FIG. 1, dosage levels 2 and 3 of the Echinacea composition described in this Example suppressed the production of IL-2 in splenocytes, while dosage levels 4 and 5 yielded a value close to that of the controls for the production of IL-2. The suppressive effect is more clearly observed in FIG. 8 which shows a plot of rat splenocyte production of IL-2 versus relative concentration of the Echinacea composition. Suppression of IL-2 results in suppression of the inflammatory response which can reduce the severity of the symptoms of inflammatory diseases (and may ameliorate the symptoms of late-onset diabetes).

As shown in FIGS. 3–5, the Echinacea cichoric acid, alkylamide and polysaccharide extracts did not affect the production of IL-2 in splenocytes.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An Echinacea composition comprising standardized amounts of cichoric acid, Echinacea alkylamides and Echinacea polysaccharides wherein said standarized amount of cichoric acid is from about 0.2 mg/ml to about 500 mg/ml, said standardized amount of Echinacea alkylamides is from about 0.02 mg/ml to about 50 mg/ml and said standardized amount of Echinacea polysaccharides is from about 10 mg/ml to about 800 mg/ml.

2. The Echinacea composition of claim 1 wherein said standardized amount of cichoric acid is from about 0.3 mg/ml to about 30 mg/ml, said standardized amount of Echinacea alkylamides is from about 0.05 mg/ml to about 50 mg/ml and said standardized amount of Echinacea polysaccharides is from about 20 mg/ml to about 800 mg/ml.

3. The Echinacea composition of claim 2 wherein said standardized amount of cichoric acid is from about 5.0 mg/ml to about 30 mg/ml, said standardized amount of Echinacea alkylamides is from about 0.8 mg/ml to about 50 mg/ml and said standardized amount of Echinacea polysaccharides is from about 50 mg/ml to about 800 mg/ml.

4. An Echinacea composition comprising standardized amounts of cichoric acid, Echinacea alkylamides and Echinacea polysaccharides wherein said standardized amount of cichoric acid is from about 15 mg/g to about 500 mg/g, said standardized amount of Echinacea alkylamides is from about 0.1 mg/g to about 100 mg/g and said standardized amount of Echinacea polysaccharides is from about 10 mg/g to about 900 mg/g.

5. The Echinacea composition of claim 4 wherein said standardized amount of cichoric acid is from about 15 mg/g to about 500 mg/g, said standardized amount of Echinacea alkylamides is from about 5 mg/g to about 100 mg/g and said standardized amount of Echinacea polysaccharides is from about 200 mg/g to about 900 mg/g.

6. The Echinacea composition of claim 1 wherein said composition is in a form selected from the group consisting of a solid, a gel and a liquid.

* * * * *

UNITED STATES PATENT AND TRADEMARK OFFICE
CERTIFICATE OF CORRECTION

PATENT NO. : 6,511,683 B1
DATED : January 28, 2003
INVENTOR(S) : R.J. Gahler et al.

It is certified that error appears in the above-identified patent and that said Letters Patent is hereby corrected as shown below:

<u>Title page, Item [54] and Column 1, line 1,</u>
"ENCHINACEA" should read -- ECHINACEA --
Item [56], References Cited, OTHER PUBLICATIONS,
"Bauer, R." reference, "*Phototherapie*" should read -- *Phytotherapie* --
3$^{rd}$ "Bauer, R." reference, "*Phototherapeutic*" should read -- *Phytotherapeutic* --
"Beucher, N. Scheit, K., Bodinet, C., and Kopanski, L.," reference,
"*Paptisia*" should read -- *Baptisia* --
After "Bukovsky" delete the second ","
After "M." insert -- , --
"Gaisbauer, …" reference, "*Research*,40:594-598" should read
-- *Research*, 40:594-598 --
"Jurcic, K., …" reference, "Echinacea--Containing" should read
-- Echinacea-Containing --
"Lohmann-Matthes, M. and Wagner, H.," reference, ""Machrophage" should read
-- "Macrophage --
"Schumacher, A., and Friedberg, K.D.," reference, "*Arzeimittle-Forschung/Drug*"
should read -- *Arzneimittle-Forschung/Drug*"
"Soicke, H., Al-Hassan, G., and Gorler, K.," reference, "54:176-176" should read
-- 54:175-176 --
"Wagner, H., Jurcic, K.," reference, "Phatocytosis,"" should read -- Phagocytosis," --
"Wagner, H., Stuppner, H., Puhlmann, J., Jurcic, K and Zenk., M.," reference,
"Pokysaccharide" should read -- Polysaccharide --
"Wagner H., Stuppner, H., Puhlmann, J., Jurcic, K., and Zenk, M.," reference,
"*Pytotherapie*," should read -- *Phytotherapie*, --
"Bauer, R., The Echinea Story…" reference, "317-3323" should read -- 317-332 --
"Bauer, R., Khan, I., Wagner, H.," reference, "*augustifolia*" should read
-- *angustifolia* --
"Bauer, R., Remiger, P., and Wagner, H., "Alkamides…" reference, "*augustifolia*"
should read -- *angustifolia* --
"Beuscher, N., Kopanski, L., and Ernwein, C.," reference, "*augustifolia*" should read
-- *angustifolia* --
"Benscher, N., Scheit, K., Bodinet, C., and Egert. D," reference, "*trinctoria*"
should read -- *tinctoria* --
"Bukovsky, M., …" reference, "*augustifolia*" should read -- *angustifolia* --

UNITED STATES PATENT AND TRADEMARK OFFICE
CERTIFICATE OF CORRECTION

PATENT NO.     : 6,511,683 B1
DATED          : January 28, 2003
INVENTOR(S)    : R.J. Gahler et al.

It is certified that error appears in the above-identified patent and that said Letters Patent is hereby corrected as shown below:

OTHER PUBLICATIONS, cont'd,
"Facino, R., Carini, M., Aldini, G., and Martinello, C., ..." reference, "*augustifolia*" should read -- *angustifolia* --
"Heinzer, F., Meusy J., and Chavanne, M.," reference, "Chromatography-Electropspray" should read -- Chromatography-Electrospray --
"Roesler, J." Emmendorffer, A., ..." reference, "Immunop-harmacology" should break as follows -- Immuno-pharmacology --
"Tragni, E., Galli, A., ..." reference, "*augustifolia*" should read -- *angustifolia* --
"Tubaro, A., Tragni, E., ..." reference, "*augustifolia*" should read -- *angustifolia* --
"Tyler, V.," reference, "*Phytochemicals*," should read -- *Phytomedicinals*, --
"Wagner, Hildebert," reference, ""Immunosimulants" should read -- "Immunostimulants --

Column 1,
Line 26, after "standardized" delete ","

Column 4,
Line 54, after "TNF-α", delete ":"

Column 5,
Line 47, "E. purpurea" should read -- *E. purpurea* --

Column 6,
Line 7, after "perlite" delete ","

Column 7,
Lines 22-23, "component (s)." should not break

Column 8,
Line 4, "800 mg/ml. more preferably" should read -- 800 mg/ml, more preferably --
Line 58, "invention).," should read -- invention), --

UNITED STATES PATENT AND TRADEMARK OFFICE
CERTIFICATE OF CORRECTION

PATENT NO. : 6,511,683 B1
DATED : January 28, 2003
INVENTOR(S) : R.J. Gahler et al.

It is certified that error appears in the above-identified patent and that said Letters Patent is hereby corrected as shown below:

Column 12,
Line 65, "*E angustifolia*" should read -- *E. angustifolia* --
Line 67, "*E pallida.*" should read -- *E. pallida.* --

Column 15,
Line 14, "only he addition" should read -- only the addition --

Column 16,
Line 49, "(e.g," should read -- (e.g., --

Column 17,
Line 32, "particles sizes" should read -- particle sizes --

Column 19,
Lines 29-30, "Spectra/Por
            ®10,000" should break as follows -- Spectra/Por®
            10,000 --
Line 47, "*Meidca,*" should read -- *Medica,* --

Column 20,
Line 39, "Meidca," should read -- Medica, --

Column 21,
Line 12, before "minimum amount" insert -- a --

Column 23,
Lines 4-5, "Echinacea purpurea" should read -- *Echinacea purpurea* --
Lines 9-15, delete Table 1 and insert therefor --

Table 1

|  | Level 1 (µg/kg) | Level 2 (µg/kg) | Level 3 (µg/kg) | Level 4 (µg/kg) | Level 5 (µg/kg) |
| --- | --- | --- | --- | --- | --- |
| Alkylamide | 0.5 | 4 | 12 | 80 | 200 |
| Cichoric Acid | 5 | 40 | 120 | 800 | 2000 |
| Polysaccharides | 125 | 1000 | 3000 | 20000 | 50000 |

--

UNITED STATES PATENT AND TRADEMARK OFFICE
CERTIFICATE OF CORRECTION

PATENT NO. : 6,511,683 B1
DATED : January 28, 2003
INVENTOR(S) : R.J. Gahler et al.

It is certified that error appears in the above-identified patent and that said Letters Patent is hereby corrected as shown below:

<u>Column 23, (cont'd),</u>
Lines 43-44, "at 30º C." should read -- at-30º C. --

<u>Column 24,</u>
Line 2, "a stock" should read -- A stock --
Lines 22 and 59, "as shown" should read -- As shown --

<u>Column 25,</u>
Lines 8, 30, 40 and 45, "as shown" should read -- As shown --

<u>Column 26,</u>
Line 16, "standarized" should read -- standardized --

Signed and Sealed this

Nineteenth Day of August, 2003

JAMES E. ROGAN
*Director of the United States Patent and Trademark Office*